(12) United States Patent
Beaupre

(10) Patent No.: US 11,420,357 B2
(45) Date of Patent: Aug. 23, 2022

(54) SYSTEM HAVING DRUM DISCHARGE OUTLET SENSORS AND METHOD OF CHARACTERIZING FRESH CONCRETE DELIVERY USING SAME

(71) Applicant: COMMAND ALKON INCORPORATED, Birmingham, AL (US)

(72) Inventor: Denis Beaupre, Québec (CA)

(73) Assignee: COMMAND ALKON INCORPORATED, Birmingham, AL (US)

( * ) Notice: Subject to any disclaimer, the term of this patent is extended or adjusted under 35 U.S.C. 154(b) by 0 days.

(21) Appl. No.: 17/043,062

(22) PCT Filed: May 2, 2019

(86) PCT No.: PCT/US2019/030312
§ 371 (c)(1),
(2) Date: Sep. 29, 2020

(87) PCT Pub. No.: WO2019/213342
PCT Pub. Date: Nov. 7, 2019

(65) Prior Publication Data
US 2021/0031408 A1    Feb. 4, 2021

Related U.S. Application Data

(60) Provisional application No. 62/665,752, filed on May 2, 2018.

(51) Int. Cl.
*B28C 5/42* (2006.01)
*G01N 33/38* (2006.01)

(52) U.S. Cl.
CPC ............ *B28C 5/422* (2013.01); *B28C 5/4248* (2013.01); *B28C 5/4268* (2013.01); *B28C 5/4272* (2013.01); *G01N 33/383* (2013.01)

(58) Field of Classification Search
CPC ..... B28C 5/422; B28C 5/4272; B28C 5/4237; B28C 5/4231; B28C 7/024; B28C 7/026;
(Continued)

(56) References Cited

U.S. PATENT DOCUMENTS 7,729,831 B2     6/2010 Pillar et al.
9,550,312 B2 *   1/2017 Roberts ................ G01N 33/383
(Continued)

FOREIGN PATENT DOCUMENTS

DE    29 24 736 A1     1/1981
WO    2014/023073 A1   2/2014

OTHER PUBLICATIONS

International Search Report and Written Opinion issued for International Application No. PCT/US2019/030312 dated Jul. 18, 2019, 8 pages.

*Primary Examiner* — Charles Cooley
(74) *Attorney, Agent, or Firm* — Rothwell, Figg, Ernst & Manbeck, P.C.

(57) ABSTRACT

The application presents a system generally having a rotatable drum rotatably for receiving fresh concrete, the drum having inwardly protruding blades mounted inside the drum which, when the drum is rotated in an unloading direction, force fresh concrete inside the drum towards a discharge outlet of the drum, at least one discharge outlet sensor disposed at the discharge outlet of the drum and being configured to sense the presence of fresh concrete at the discharge outlet as the drum rotates in the unloading direction; and a controller communicatively coupled with the at least one discharge outlet sensor, the controller being configured for performing the steps of: receiving a signal from the at least one discharge outlet sensor indicative of the presence of the discharged fresh concrete at the discharge outlet as the drum rotates in the unloading direction; and
(Continued)

*1500*

| Discharge a volume of the fresh concrete from the drum by rotating the drum in the unloading direction while monitoring a given number of unloading rotations | —1502 |

↓

| Monitor the presence of the discharged fresh concrete at the discharge outlet as the drum rotates in the unloading direction using at least one sensor disposed at the discharge outlet of the drum | —1504 |

↓

| Determine at least one parameter characterizing the delivery of the fresh concrete using the mixer truck based on the given number of unloading rotations and on said monitoring | —1506 | determining at least one parameter based on the received signal.

13 Claims, 15 Drawing Sheets

(58) Field of Classification Search
CPC ..... B28C 7/022; B28C 5/4217; B28C 5/4244; B28C 5/4268; B28C 5/18; B28C 5/42; B28C 7/16; B28C 5/4248; B28C 7/02; G01N 2011/0046; G01N 11/14; G01N 33/383; G01N 33/38
See application file for complete search history.

(56) References Cited

U.S. PATENT DOCUMENTS

| | | | | |
|---|---|---|---|---|
| 10,363,684 B2 * | 7/2019 | Roberts | .................. | G01N 11/00 |
| 10,520,410 B2 * | 12/2019 | Beaupre | .................. | G01N 11/10 |
| 10,987,829 B2 * | 4/2021 | Datema | .................. | G06Q 50/08 |
| 10,989,643 B2 * | 4/2021 | Beaupre | ............... | G01N 33/383 |
| 11,123,896 B2 * | 9/2021 | Beaupre | .................. | B28C 5/0812 |
| 11,224,989 B2 * | 1/2022 | Beaupre | .................. | B28C 5/4217 |
| 11,230,217 B2 * | 1/2022 | Beaupre | .................. | B28C 5/422 |
| 11,273,575 B2 * | 3/2022 | Roberts | .................. | B28C 5/422 |
| 11,275,009 B2 * | 3/2022 | Biesak | .................. | G01N 33/383 |
| 11,275,073 B2 * | 3/2022 | Lehner | .................... | G01S 13/88 |
| 2014/0104972 A1 * | 4/2014 | Roberts | .................. | B28C 7/0454 366/2 |
| 2015/0355160 A1 * | 12/2015 | Berman | .................. | G01N 11/14 73/54.03 |
| 2017/0087743 A1 * | 3/2017 | Roberts | .................... | F24F 13/32 |
| 2017/0108421 A1 * | 4/2017 | Beaupre | .................. | G01N 11/10 |
| 2019/0204197 A1 * | 7/2019 | Beaupre | .................. | G01N 29/00 |
| 2019/0242802 A1 * | 8/2019 | Beaupre | .................. | G01N 11/10 |
| 2020/0078987 A1 * | 3/2020 | Beaupre | .................. | G01N 11/14 |
| 2020/0225258 A1 * | 7/2020 | Beaupre | ..................... | G01P 3/48 |
| 2020/0232966 A1 * | 7/2020 | Beaupre | ............... | G01N 33/383 |
| 2020/0282597 A1 * | 9/2020 | Beaupre | .................. | B28C 5/422 |
| 2021/0001765 A1 * | 1/2021 | Beaupre | .................. | B28C 5/422 |
| 2021/0031407 A1 * | 2/2021 | Roberts | .................. | B28C 5/4231 |
| 2021/0031408 A1 * | 2/2021 | Beaupre | .................. | B28C 5/422 |
| 2021/0055195 A1 * | 2/2021 | Beaupre | .................. | B28C 7/024 |
| 2021/0187786 A1 * | 6/2021 | Beaupre | .................. | B28C 5/422 |
| 2021/0394394 A1 * | 12/2021 | Datema | .................. | B28C 5/4217 |
| 2022/0034724 A1 * | 2/2022 | Cathcart | .................. | G01D 21/02 |

\* cited by examiner

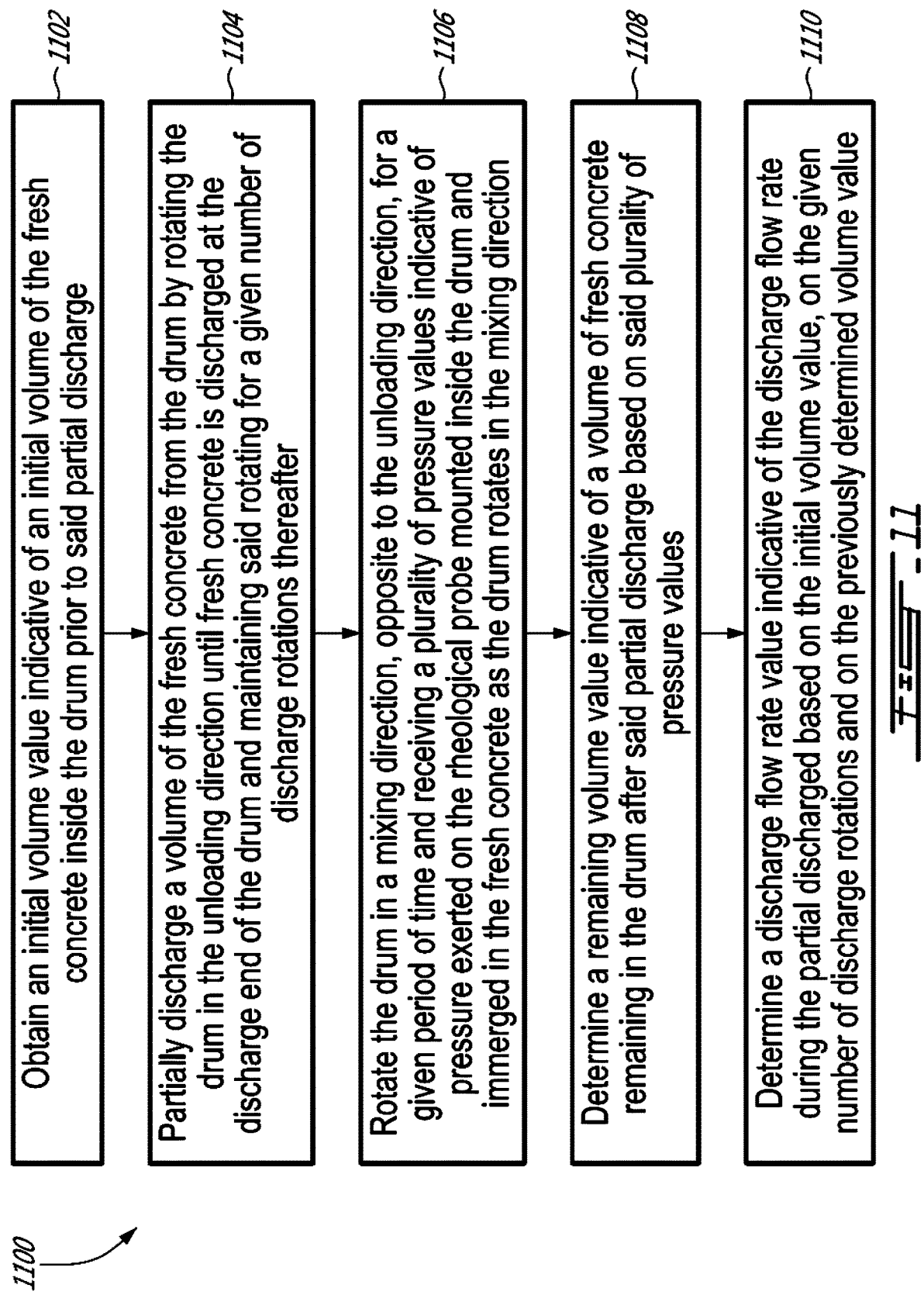

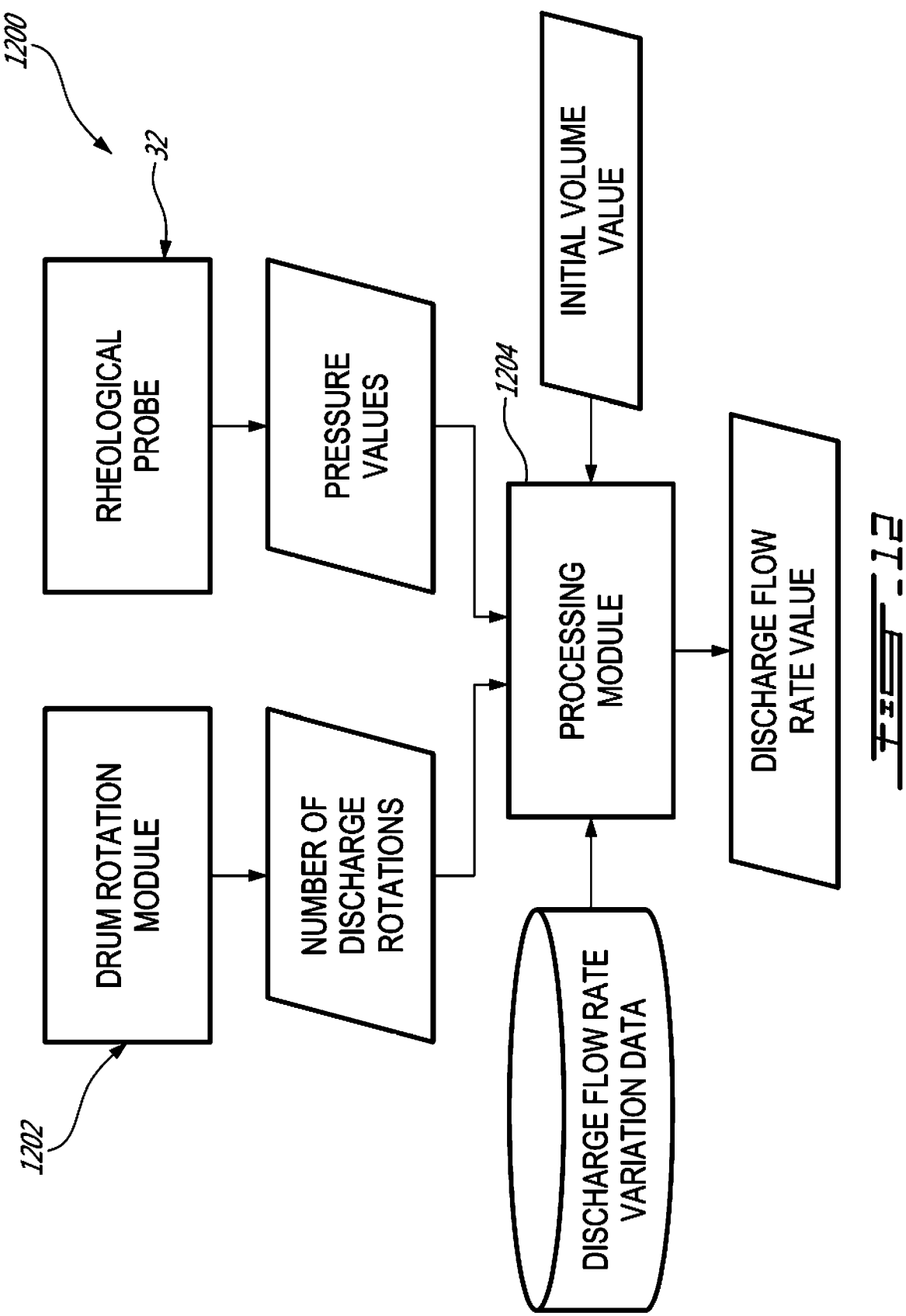

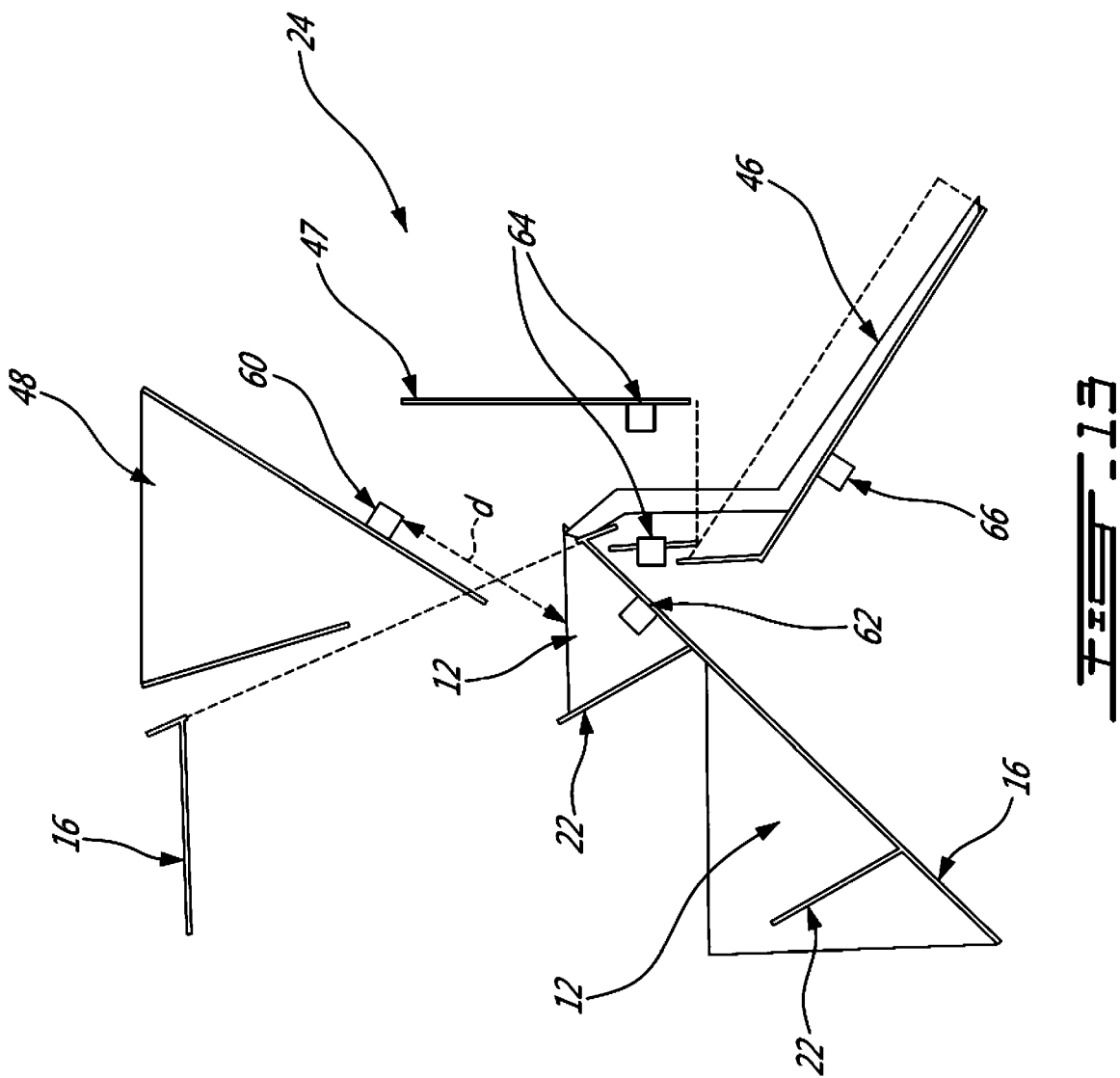

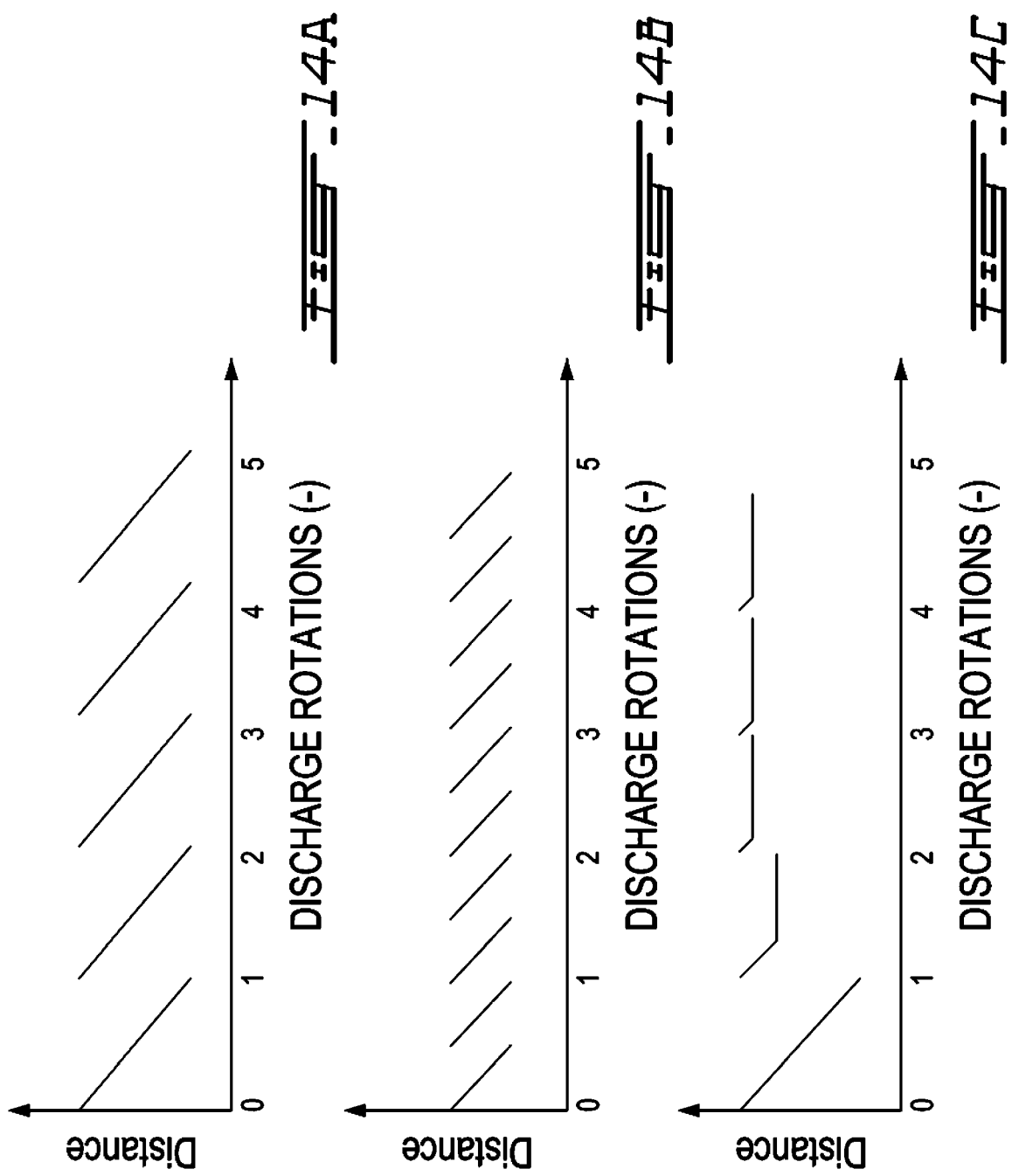

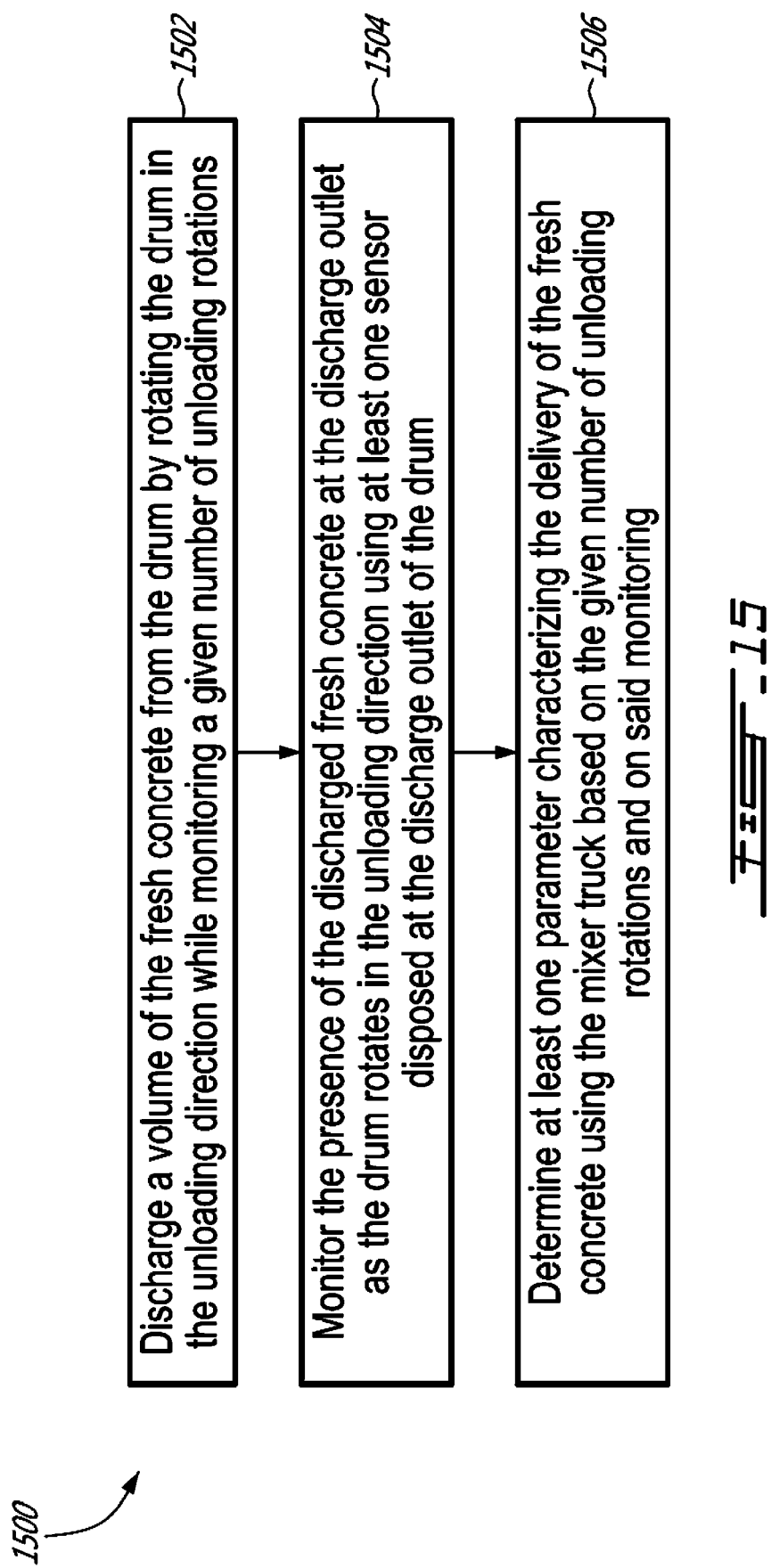

SYSTEM HAVING DRUM DISCHARGE OUTLET SENSORS AND METHOD OF CHARACTERIZING FRESH CONCRETE DELIVERY USING SAME

CROSS-REFERENCE TO RELATED APPLICATION

This application is 35 U.S.C. 371 National Phase Entry Application of PCT/US2019/030312, filed May 2, 2019, which claims the benefit of priority of U.S. Provisional Patent Application No. 62/665,752, filed May 2, 2018, which is hereby incorporated by references in their entirety.

FIELD

The improvements generally relate to the field of concrete production, and more particularly relate to the delivery of fresh concrete using mixer trucks.

BACKGROUND

A mixer truck generally has a frame and a drum which is rotatably mounted to the frame. Typically, the drum has inwardly protruding blades mounted therein which, depending on whether the drum is rotated in a mixing direction or in an unloading direction, either mix the concrete constituents or force freshly mixed concrete constituents, i.e. the fresh concrete, towards a discharge outlet of the drum. Accordingly, the mixer truck can carry a volume of fresh concrete from a concrete production site to one or more construction sites where it can be poured as desired.

In some circumstances, only a fraction of the volume of fresh concrete initially carried in the drum may be discharged at a first construction site. In these circumstances, knowledge concerning the amount of fresh concrete which remain inside the drum after the partial discharge at the first construction site can be advantageously used. For instance, the remaining amount of fresh concrete can be discharged at a second construction site. Alternately, the mixer truck can be instructed to return to the concrete production site should the remaining amount of fresh concrete be insufficient for an additional discharge.

Examples of conventional techniques for evaluating the remaining amount of fresh concrete inside the drum after a partial discharge are described in U.S. Pat. No. 5,752,768 to Assh, U.S. Pat. No. 9,550,312 B2 to Roberts et al. In these conventional techniques, the remaining amount of fresh concrete inside the drum after a partial discharge is determined based on an initial amount of fresh concrete in the drum, a number of rotations of the drum in the unloading direction and a discharge flow rate value using an equation equivalent to:

$$V_R = V_I - DFR \cdot (N_T - N_P);$$

where $V_R$ denotes the remaining amount of fresh concrete in the drum after the partial discharge, $V_I$ denotes the initial amount of fresh concrete initially inside the drum, DFR denotes the discharge flow rate, i.e. the volume of fresh concrete that is discharged at the discharge outlet of the drum per discharge rotation, $N_T$ denotes a total number of rotations in the unloading direction and $N_P$ denotes a priming number of discharge rotations indicative of the number of rotations of the drum in the unloading direction which are required so that fresh concrete be discharged at the discharge outlet of the drum. As can be appreciated, other authors may use other similar expressions such as "discharge rate per turn" or "volume-per-revolution-upon-discharge" to refer to the discharge flow rate.

Although such techniques have been found to be satisfactory to a certain degree, there remains room for improvement.

SUMMARY

The inventor found drawbacks associated to existing methods for determining the discharge flow rate and/or methods of determining the priming number $N_p$ of discharge rotations, as they generally required an operator to look at the discharge outlet of the drum in order to determine whether fresh concrete is being discharged or not.

In accordance with one aspect, there is provided a system comprising: a frame; a drum rotatably mounted to the frame for receiving fresh concrete, the drum having inwardly protruding blades mounted inside the drum which, when the drum is rotated in an unloading direction, force fresh concrete inside the drum towards a discharge outlet of the drum; at least one discharge outlet sensor disposed at the discharge outlet of the drum and being configured to sense the presence of fresh concrete at the discharge outlet as the drum rotates in the unloading direction; and a controller communicatively coupled with the at least one discharge outlet sensor, the controller being configured for performing the steps of: receiving a signal from the at least one discharge outlet sensor indicative of the presence of the discharged fresh concrete at the discharge outlet as the drum rotates in the unloading direction; and determining at least one parameter based on the received signal.

In accordance with another aspect, there is provided a method for determining at least one parameter characterizing delivery of fresh concrete using a mixer truck, the mixer drum having a rotatable drum having inwardly protruding blades mounted inside the drum which, when the drum is rotated in an unloading direction, force the fresh concrete towards a discharge outlet of the drum, the method comprising: discharging a volume of the fresh concrete from the drum by rotating the drum in the unloading direction while monitoring a given number of unloading rotations; using at least one discharge outlet sensor disposed at the discharge outlet of the drum, monitoring the presence of the discharged fresh concrete at the discharge outlet as the drum rotates in the unloading direction; and determining at least one parameter characterizing the delivery of the fresh concrete using the mixer truck based on the given number of unloading rotations and on said monitoring.

It will be understood that the expression "computer" as used herein is not to be interpreted in a limiting manner. It is rather used in a broad sense to generally refer to the combination of some form of one or more processing units and some form of memory system accessible by the processing unit(s). Similarly, the expression "controller" as used herein is not to be interpreted in a limiting manner but rather in a general sense of a device, or of a system having more than one device, performing the function(s) of controlling one or more device such as an electronic device or an actuator for instance.

It will be understood that the various functions of a computer or of a controller can be performed by hardware or by a combination of both hardware and software. For example, hardware can include logic gates included as part of a silicon chip of the processor. Software can be in the form of data such as computer-readable instructions stored in the memory system. With respect to a computer, a controller, a processing unit, or a processor chip, the expression "configured to" relates to the presence of hardware or a combination of hardware and software which is operable to perform the associated functions.

Many further features and combinations thereof concerning the present improvements will appear to those skilled in the art following a reading of the instant disclosure.

DESCRIPTION OF THE FIGURES

In the figures,

FIG. 11 is a flowchart of an example of a method for determining a discharge flow rate of fresh concrete being discharged by the drum of FIG. 1, in accordance with an embodiment;

FIG. 12 is a schematic view of an example of a software application of the controller of FIG. 1 being configured to perform the method of FIG. 11, in accordance with an embodiment;

FIG. 13 is an enlarged view of a discharge outlet of the drum of FIG. 1, showing discharge outlet sensors, in accordance with an embodiment;

FIGS. 14A-C show graphs of distance from one of the inwardly protruding blades of the drum as received from one of the discharge outlet sensors of FIG. 13, in accordance with an embodiment; and FIG. 15 is a flowchart of an example of a method for determining one or more parameters characterizing the delivery of the fresh concrete based on signal received from the discharge outlet sensors of FIG. 13.

DETAILED DESCRIPTION

Figure 1:
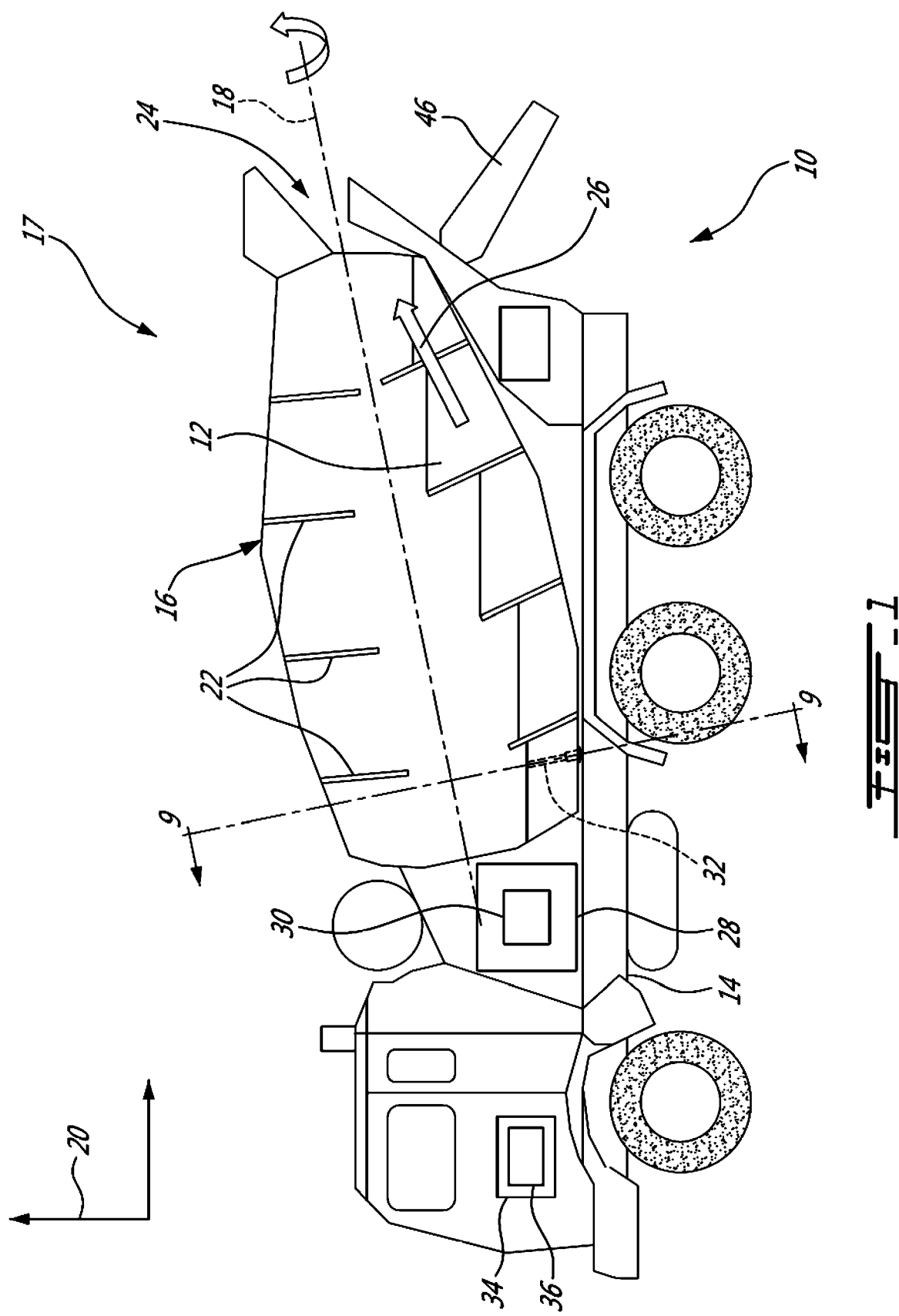
FIG. 1 is a side view of an example of a system having a rotating drum, showing a sectional view of the drum, in accordance with an embodiment.

FIG. 1 shows an example of a system 10 for delivering fresh concrete 12. As depicted, the system 10 includes a frame 14 and a drum 16 containing the fresh concrete 12. In this specific example, the frame 14 is part of a mixer truck 17. As shown, the drum 16 is rotatably mounted to the frame 14 so as to be rotatable about a rotation axis 18 which is in this example at least partially horizontally-oriented relative to the vertical 20.

As illustrated, the drum has inwardly protruding blades 22 mounted inside the drum 16 which, when the drum 16 is rotated in an unloading direction, force the fresh concrete 12 along discharge direction 26 towards a discharge outlet 24 of the drum 16 so as to be poured where desired.

In contrast, when the drum 16 is rotated in a mixing direction, opposite to the unloading direction, the fresh concrete 12 is kept and mixed inside the drum 16. For instance, in some embodiments, concrete constituents (e.g., cement, aggregate and water) can be loaded in the drum 16 after which the drum 16 can be rotated a certain number of rotations in the mixing direction at a certain rotation speed so as to suitably mix the concrete constituents to one another, thus yielding the fresh concrete 12. In other embodiments, already mixed fresh concrete is loaded inside the drum 16 for delivery, in which case the fresh concrete 12 can still be further mixed inside the drum 16 before discharging.

As shown, the system 10 has a driving device 28 mounted to the frame 14 for driving rotation of the drum 16 using a hydraulic fluid. In this example, the hydraulic fluid can be oil (e.g., mineral oil), water and the like. A hydraulic pressure sensor 30 can be mounted to the driving device 28 for measuring hydraulic pressure values indicative of the pressure of hydraulic fluid as it is used to drive rotation of the drum 16.

In this specific embodiment, a rheological probe 32 can be mounted inside the drum 16 so as to be immerged in the fresh concrete 12 as the drum 16 rotates. In this embodiment, the rheological probe 32 can measure a plurality of probe pressure values indicative of pressure exerted on the rheological probe 32 by the fresh concrete 12 as the drum 16 rotates. A potential example of the rheological probe 32 is described in international patent publication no. WO 2011/042880.

In some embodiments, the hydraulic pressure sensor 30, the rheological probe 32 and/or any other suitable rotation sensor can be used to sense and/or monitor a circumferential position of the drum 16, a number of rotations of the drum 16 and/or a rotation direction of these rotations. For instance, the number of rotations of the drum 16 in the mixing direction and/or the number of rotations of the drum 16 in the unloading direction can be monitored over time. Of course, the number of rotations can be monitored in terms of integer number of rotations or in terms of fractional number of rotations.

Still referring to FIG. 1, the system 10 has a controller 34 which is communicatively coupled at least with the hydraulic pressure sensor 30 and with the rheological probe 32. The communication between the controller 34 and the driving device 28 can be provided by a wireless connection, a wired connection, or a combination thereof. Similarly, the communication between the controller 34 and the hydraulic pressure sensor 30 and/or the rheological probe 32 can be provided by a wireless connection, a wired connection, or a combination thereof.

In this specific embodiment, the system 10 has a user interface 36 which is communicatively coupled with the controller 34. As can be understood, the user interface 36 can be used to receive inputs and/or display data.

Examples of inputs that can be received via the user interface 36 can include an indication of a workability (e.g., type of, slump, viscosity value, viscosity range) of the fresh concrete 12 inside the drum 16, an indication of a volume of fresh concrete 12 that is initially loaded in the drum 16 at the concrete production plant, an indication of the number of rotations to be made in the mixing direction, an indication of the number of rotations to be made in the unloading direction and/or an indication of a rotation speed of the drum 16.

Examples of data that can be displayed by the user interface 36 can include the number of rotations in the unloading rotations made since rotation has been initiated, pressure probe values received from the rheological probe 32, hydraulic pressure values received from the hydraulic pressure sensor 30, and/or workability values indicative of the workability of the fresh concrete 12 inside the drum as determined using the hydraulic pressure sensor 30 and/or the rheological probe 32.

In this disclosure, rotations of the drum in the mixing direction are referred to as mixing rotations whereas rotations of the drum in the unloading direction can be referred either to as unloading rotations or discharge rotations. More specifically, unloading rotations are the rotations of the drum during which the fresh concrete 12 is carried towards the discharge outlet 24 of the drum and prior to actual discharge of the fresh concrete 12. In contrast, discharge rotations are the rotations of the drum during which the fresh concrete 12 is actually discharging at the discharge outlet 24. Accordingly, once the unloading rotations end, the discharge rotations begin. The number of unloading rotations are sometimes referred to as the priming number in the industry.

As described above, the remaining amount $V_R$ of the fresh concrete 12 inside the drum 16 after a partial discharge can be determined based on the initial amount $V_I$ of the fresh concrete 12 in the drum 16, the number $N_d$ of discharge rotations of the drum 16 in the unloading direction and the discharge flow rate value DFR using an equation equivalent to:

$$V_R = V_I - DFR \cdot (N_T - N_p) = V_I - DFR \cdot N_d.$$

The initial amount $V_I$ of the fresh concrete 12 in the drum 16 is generally known from the concrete production plant. For instance, in some circumstances, the initial amount $V_I$ of the fresh concrete 12 is constant for a given type of applications. In other circumstances, the initial amount $V_I$ of the fresh concrete 12 loaded inside the drum 16 is measured during the loading and then communicated to the system 10, or alternatively inputted via the user interface 36 by a driver or when received from a batch or dispatch system.

Determining when the unloading rotations end and when the discharge rotations begin, and determining the discharge flow rate value DFR during the discharge rotations can be more challenging.

For instance, in many situations, determining these parameters is performed as following. First, a known initial amount $V_I$ of the fresh concrete 12 is loaded in the drum 16. Then, the rotation of the drum 16 in the unloading rotation is initiated and an operator monitors the number of the rotations of the drum 16 over time. When the operator notices the fresh concrete 12 actually reaches the discharge outlet 24 of the drum 16, the operator records the number of rotations since the rotation of the drum 16 has been initiated, which represents the number $N_p$ of unloading rotations, or priming number. Ultimately, as the rotation of the drum 16 continues, the totality of the fresh concrete 12 inside the drum 16 will be discharged, in which case the operator records the total number $N_T$ of rotations required for the total discharge. In this case, the number $N_d$ of discharge rotations is the difference between the total number $N_T$ of rotations and the number of unloading rotations $N_p$, i.e., $N_d = N_T - N_p$.

Figure 2:
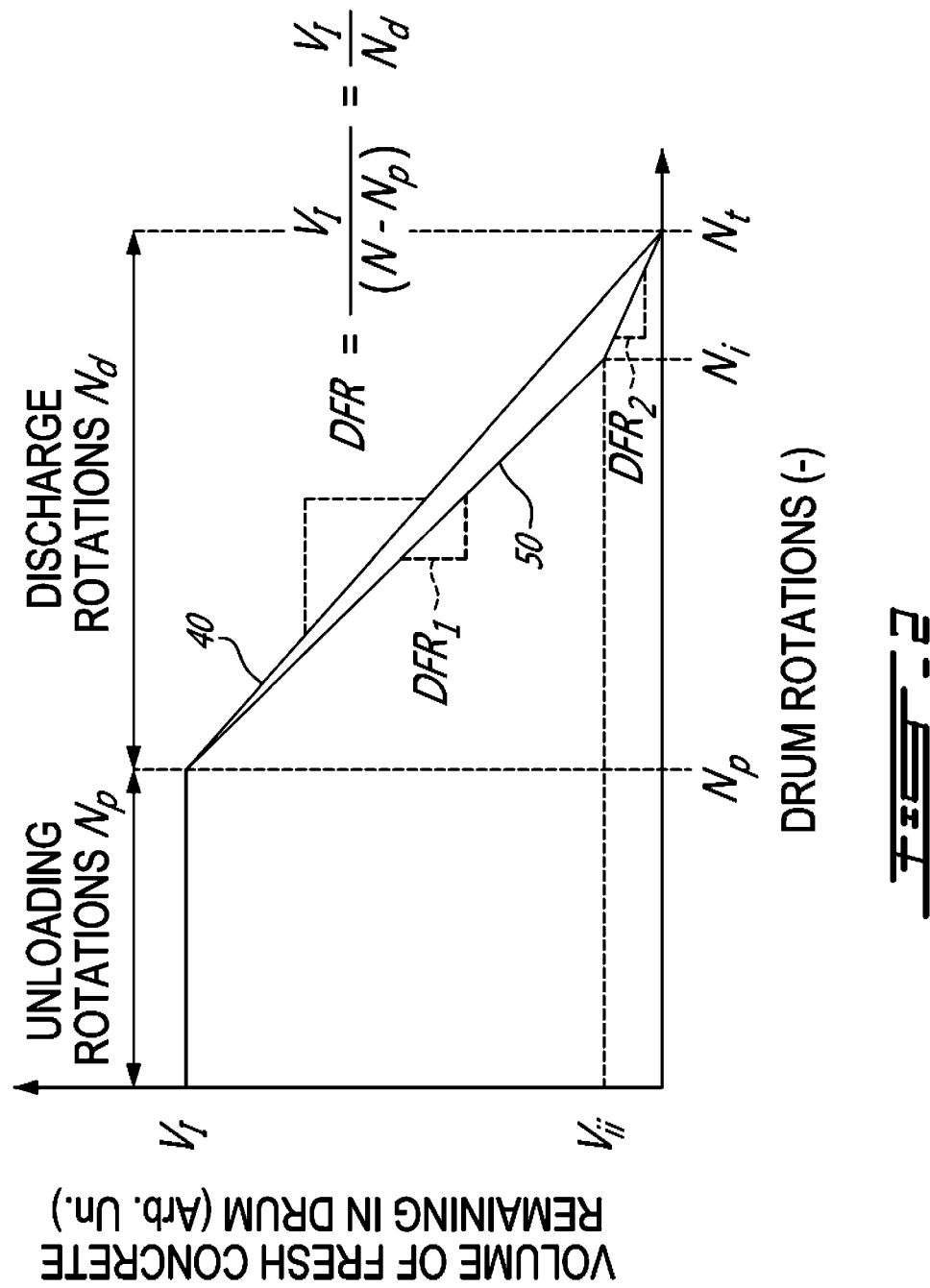
FIG. 2 is a graph showing volume of fresh concrete remaining inside the drum of FIG. 1 as function of rotations of the drum, in accordance with an embodiment.

FIG. 2 is a graph showing a relation 40 including the data points recorded by the operator during the total discharge discussed above. As shown, the volume of the fresh concrete remains constant during the unloading rotations, and begins to decrease as the unloading rotations are followed by the discharge rotations. In the industry, the discharge flow rate value DFR is estimated to be constant throughout the discharge rotations. Accordingly, determining the discharge flow rate value DFR is relatively straightforward based on the number of discharge rotations and on the initial amount of $V_I$ of the fresh concrete 12, i.e.

$$DFR = \frac{N_d}{V_I} = \frac{(N_T - N_p)}{V_I}.$$

After these determinations, the so-determined number of unloading rotations $N_p$ and the so-determined discharge flow rate value DFR are typically used for subsequent partial discharge using the same mixer truck, another mixer truck of the same type and/or other mixer trucks of other types.

Some patent documents, including the Assh Patent and the Roberts Patent referenced above, describe that such techniques have at least some drawbacks, including the fact that the number $N_p$ of unloading rotations and the discharge flow rate value DFR can vary from one mixer truck to another, based on the tilt of the mixer truck 17, on the type of blades 22 in the drum 16, on the composition of the fresh concrete 12 at the time of discharge and so forth. Although such variations were known, the discharge flow rate value DFR was still considered to be constant during the discharge rotations.

Figure 3:
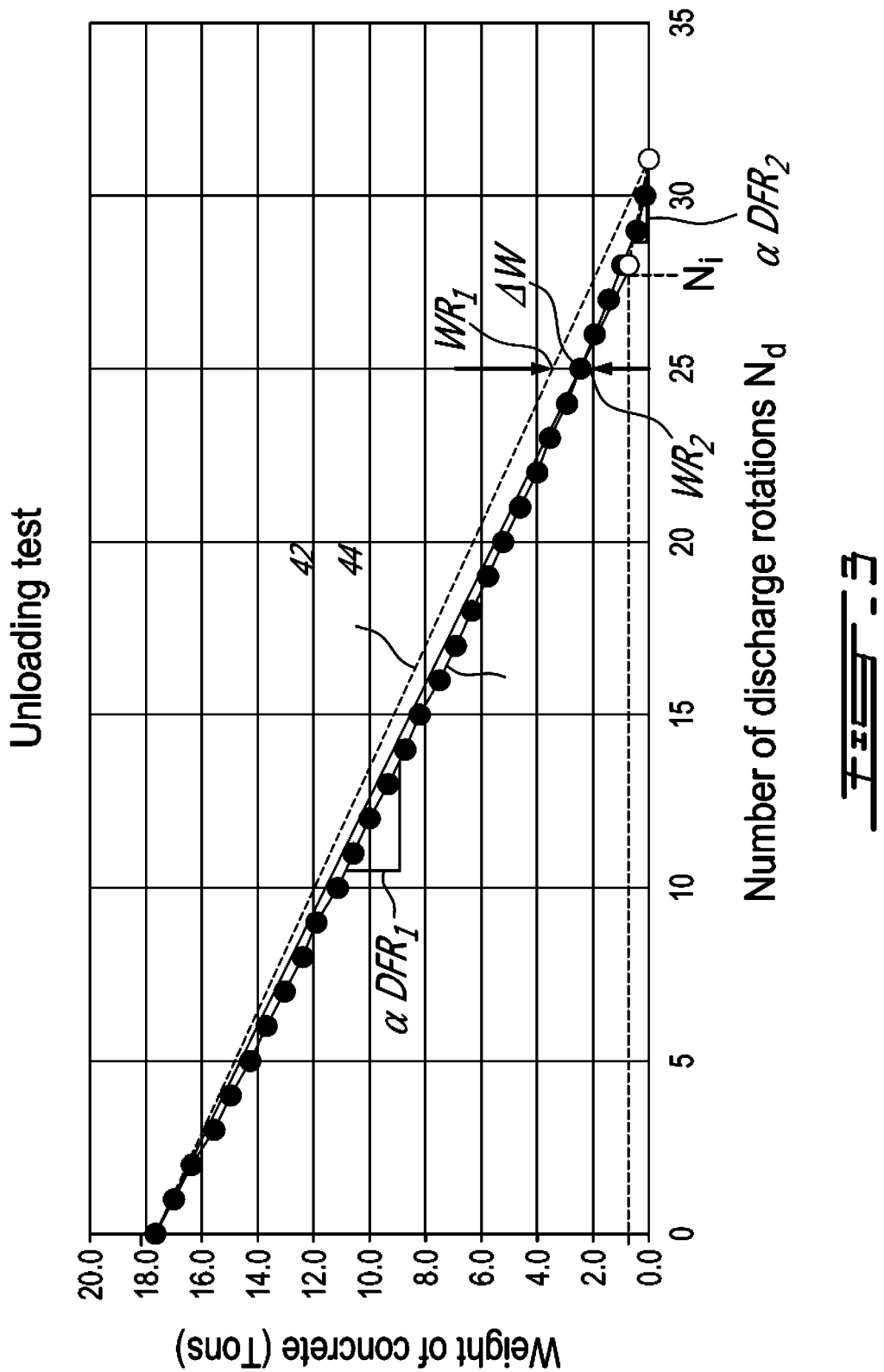
FIG. 3 is a graph showing weight of fresh concrete inside the drum of FIG. 1 as function of discharge rotations of the drum, in accordance with an embodiment.

However, the inventor found that it is in fact not the case as the discharge flow rate varies as function of the discharge rotations during a discharge, as exemplified by the graph of FIG. 3 which shows the amount of fresh concrete inside the drum 16 as function of the number $N_d$ of discharge rotations. It is noted that the data relating to the unloading rotations have been omitted in this graph. More specifically, relation 42 shows the weight of the fresh concrete 12 as would be estimated using the existing technique described above. In contrast, experimental tests were performed to determine relation 44, which represents the weight of the fresh concrete 12 inside the drum 16 as function of the number $N_d$ of discharge rotations. In this example, a volume value or a discharge flow rate value can be obtained from the weight value by converting the weight value into a volume value using a density ρ of the fresh concrete 12.

As it can be appreciated from the relation 44, the discharge flow rate varies as function of the discharge rotations. Accordingly, if a partial discharge requires 25 discharge rotations, the existing technique would have estimated the remaining amount $W_{R1}$ of fresh concrete 12 inside the drum 16 to greater than it actually is. For instance, taking into consideration the variation in the discharge flow rate during the discharge rotations, the inventor found that the remaining amount $W_{R2}$ of fresh concrete would differ from the remaining amount $W_{R1}$ by a difference in discharged amount ΔW of fresh concrete. In this case, this difference can amount to a volume difference of $\Delta V = 0.54$ yd$^3$ of fresh concrete, which can be significant, for fresh concrete having a standard density ρ.

However, the difference ΔV can be significant. For instance, industry standard such as ASTM C-1798 which is recognized in the industry requires the remaining amount of fresh concrete after a partial discharge to be known with a precision of ±0.25 yd$^3$ to allow selling of the remaining amount of fresh concrete inside the drum 16 after that partial discharge. Accordingly, taking into consideration the variation of the discharge flow rate as function of the discharge rotations can increase the precision with which the remaining amount of fresh concrete inside the drum 16 after a partial discharge is determined, it can in turn allow one or many other partial discharges to be sold, which can both increase profitability and reduce waste.

Indeed, as fresh concrete is usually sold by volume or more precisely by load of a certain volume, a customer usually orders more fresh concrete than what is needed to complete a pour at a construction site. As a result, the last mixer truck on the construction site is not always emptied completely. There is thus very often some fresh concrete left in the drum of the last mixer truck when it leaves the construction site, which can justify the use of the methods and systems described herein in at least some situations.

The inventor has found at least a few reasons for which the discharge flow rate is not constant throughout discharge. For instance, in some embodiments, the discharge flow rate is reduced near the end of the discharge process and is therefore not fully constant trough out a single discharge. In some other embodiments, the amount of hardened concrete struck between the inwardly protruding blades 22 can cause the discharge flow rate to be reduced when concrete is stuck between the inwardly protruding blades 2, like an obstruction in a pipeline, and this may cause a sudden flow rate variation from one delivery to another. In alternate embodiments, the wear of the inwardly protruding blades 22 which worn very slowly out with time can cause the discharge flow rate to decrease when concrete wear the inwardly protruding blades 22, thus requiring adjusting the discharge flow rate during the life of the drum. The rotation speed during the discharge process may affect the discharge flow rate as well.

Figure 4:
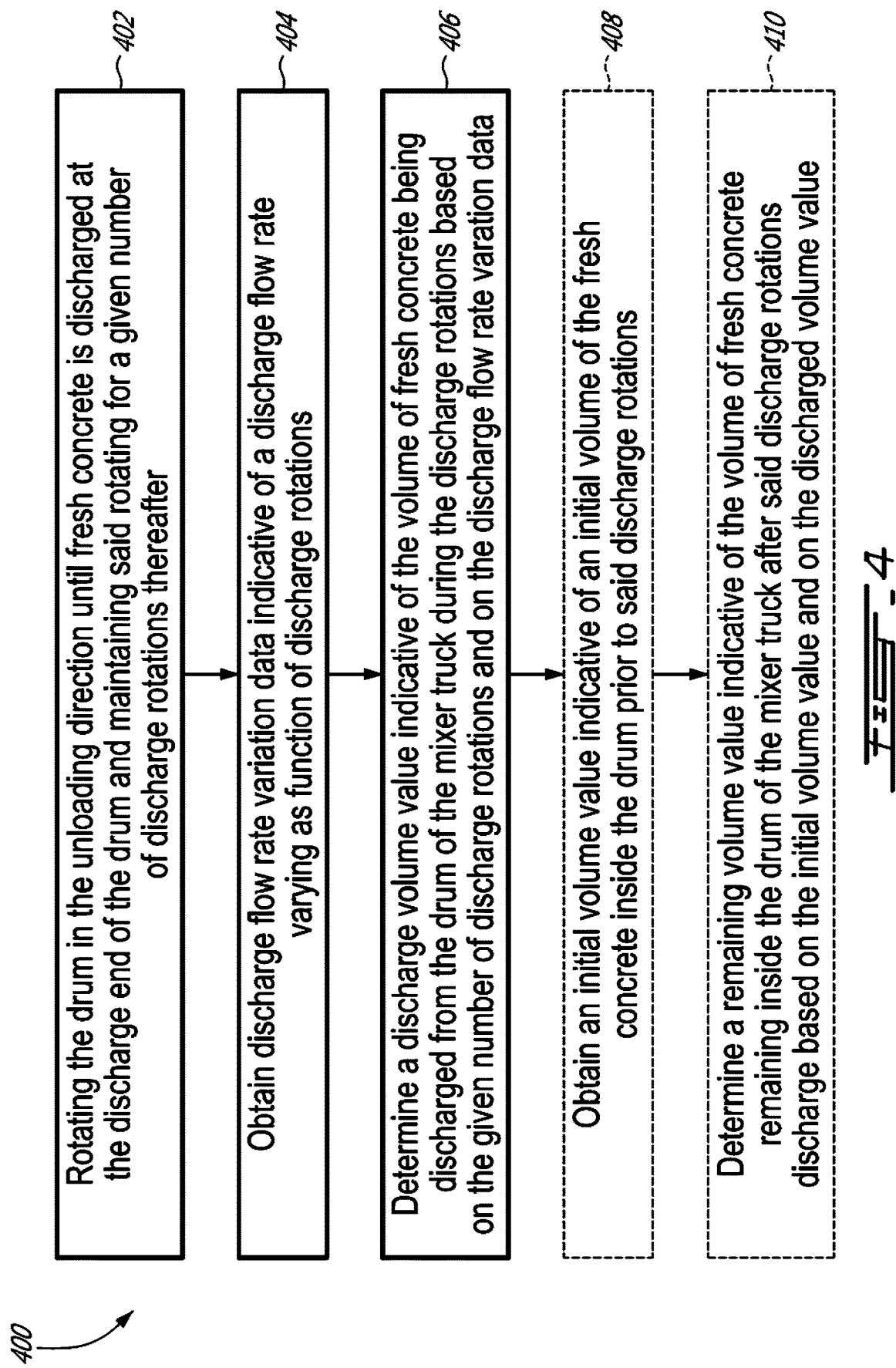
FIG. 4 is a flowchart of an example of a method for determining remaining volume of fresh concrete inside the drum of FIG. 1, in accordance with an embodiment.

Referring now to FIG. 4, there is described a method 400 for determining a volume of the fresh concrete 12 being discharged from the drum 16 of the mixer truck 17 during a partial discharge. As can be understood, the method 400 can be performed by the controller 34 and is described with reference to the system 10 of FIG. 1 for ease of reading.

At step 402, the controller 34 instructs the driving device 28 to partially discharge a volume of the fresh concrete 12 from the drum 16 by rotating the drum 16 in the unloading direction until fresh concrete is discharged at the discharge outlet 24 of the drum 16 and maintaining said rotating for a given number $N_d$ of discharge rotations thereafter.

As discussed, the given number $N_d$ of discharge rotations starts when fresh concrete 12 is actually being discharged at the discharge outlet 24. The rotation can be maintained for a predetermined number of discharge rotations or can be maintained until reception of a signal, e.g., received from the user interface 36, which would instruct the end of the partial discharge.

At step 404, the controller 34 obtains discharge flow rate variation data DFR($N_d$) indicative of a discharge flow rate DFR varying as function of the number $N_d$ of discharge rotations in which the discharge flow rate DFR is indicative of a volume of discharged fresh concrete per discharge rotation.

As can be understood, in some embodiments, the discharge flow rate variation data DFR($N_d$) are stored on a memory accessible by the controller 34. In some other embodiments, the discharge flow rate variation data DFR($N_d$) are stored on a remote memory which is accessible via a network such as the Internet, for instance. The discharge flow rate variation data DFR($N_d$) can alternatively be inputted via the user interface 36.

At step 406, the controller 34 determines a discharged volume value $V_d$ indicative of the volume of fresh concrete which has been discharged from the drum 16 of the mixer truck 17 during said partial discharge of step 402 based on the given number $N_d$ of discharge rotations and on the discharge flow rate variation data DFR($N_d$).

As can be understood, the method 400 can also be used to determine a remaining volume $V_R$ of fresh concrete 12 inside the drum 16 after the partial discharge. If desired, the controller 34 can obtain an initial volume value $V_I$ which is indicative of an initial volume of the fresh concrete 12 inside the drum 16 prior to the partial discharge and then determine the remaining volume value $V_R$ indicative of the volume of fresh concrete remaining inside the drum 16 of the mixer truck 17 after the partial discharge based on the initial volume value $V_I$ and on the discharged volume value $V_d$, as shown at steps 408 and 410.

The initial volume value $V_I$ can be provided by a batch/dispatch system or measured using the hydraulic pressure sensor 30 and/or the rheological probe 32. Alternatively, the initial volume value $V_I$ can be inputted via the user interface 36.

The discharge flow rate variation data DFR($N_d$) can vary from one embodiment to another. For instance, in some embodiments, the discharge flow rate variation data DFR($N_d$) include a plurality of discharge flow rate values $DFR_i$ each being associated to a corresponding range of discharge rotations. In some alternate embodiments, the discharge flow rate variation data DFR($N_d$) include at least a first discharge flow rate value $DFR_1$ which is indicative of the volume of fresh concrete discharged at the discharge outlet 24 per discharge rotation, and a second discharge flow rate value $DFR_2$ which is indicative of the volume of fresh concrete discharged at the discharge outlet 24 per discharge rotation. In this case, the first discharge flow rate value $DFR_1$ is different from the second discharge flow rate value $DFR_2$ so as to provide a variation in the discharge flow rate as the number $N_d$ of discharge rotations progresses during the partial discharge.

In these embodiments, the first discharge flow rate value $DFR_1$ is associated to a first range of discharge rotations, and the second discharge flow rate value $DFR_2$ is associated to a second range of discharge rotations subsequent to the first range of discharge rotations, in which case the step 406 can include calculating the discharged volume value $V_d$ using a relation equivalent to the following relation:

$$V_D = DFR_1 N_{R1} + DFR_2 N_{R2},$$

where $N_{R1}$ denotes a portion of the given number $N_d$ of discharge rotations comprised in the first range of discharge rotations, and $N_{R2}$ denotes a portion of the given number $N_d$ of discharge rotations comprised in the second range of discharge rotations.

In these embodiments, the first and second discharge flow rate values $DFR_1$ and $DFR_2$ can be pre-determined values obtained from calibration, pre-determined values based on the composition of the fresh concrete, and the like. As will be described below, the first discharge flow rate values $DFR_1$ can be measured on the go based on an intermediate volume measurement performed using probe pressure values obtained from the rheological probe 32.

Similarly, in this case, the remaining volume value $V_R$ of fresh concrete 12 inside the drum 16 after the partial discharge can be calculated using a relation equivalent to the following relation:

$$V_R = V_I - DFR_1 N_{R1} - DFR_2 N_{R2}.$$

For instance, in this example an upper limit of the first range of discharge rotations and the lower limit of the second range of discharge rotations are given by an intermediate number $N_i$ of discharge rotations. In this way, the first discharge flow rate value $DFR_1$ can be effective in the range $0 < N_d < N_i$ whereas the second discharge flow rate value $DFR_2$ can be effective in the range $N_d > N_i$.

Referring back to FIG. 3, the first discharge flow rate value $DFR_1$ can be determined based on a relation equivalent to the following relation:

$$DFR_1 = \frac{(W_I - W_i)}{\rho N_i},$$

wherein $\rho$ denotes the density of the fresh concrete 12, $W_I$ denotes the initial weight of fresh concrete inside the drum 16, $W_i$ denotes the weight of fresh concrete inside the drum 16 once the intermediate number $N_i$ of discharge rotations has been performed, and $N_i$ denotes the intermediate number $N_i$ of discharge rotations where the variation of discharge flow rate is observable.

Similarly, the second discharge flow rate value $DFR_2$ can be determined based on a relation equivalent to the following relation:

$$DFR_2 = \frac{W_i}{\rho(N_T - N_i)},$$

wherein $\rho$ denotes the density mass of the fresh concrete, $W_i$ denotes the weight of fresh concrete inside the drum 16 once the intermediate number $N_i$ of discharge rotations has been performed, and $N_T$ denotes the total number of discharge rotations.

These calculation example are provided as examples only. Other embodiments may apply.

Referring back to FIG. 2, the graph shows the remaining volume value $V_R$ of fresh concrete as function of the discharge rotations. More specifically, relation 50 takes into consideration such discharge flow rate variation data $DFR(N_d)$ whereas relation 40 does not as it involves a single discharge flow rate throughout the discharge rotations such as in the existing techniques. As can be seen, considering the variation in discharge flow rate as function of the discharge rotations can offer significant improvements.

It is noted that the first discharge flow rate value $DFR_1$ is generally greater than the second discharge flow rate value $DFR_2$, as the efficiency of the inwardly protruding blades 22 decreases with a decreasing volume of the fresh concrete inside the drum 16. In some embodiments, the intermediate number $N_i$ of discharge rotations can be estimated to be a given percentage of the total number $N_T$ of discharge rotations. For instance, the intermediate number $N_i$ of discharge rotations can be set to 90% of the total number $N_T$ of discharge rotations. In this case, once 90% of the total number $N_T$ of discharge rotations has been reached, the effective discharge flow rate changes from the first discharge flow rate value $DFR_1$ to the second discharge flow rate value $DFR_2$.

In some embodiments, the intermediate number $N_i$ of discharge rotations is received from a computer-readable memory which is part or in remote communication with the controller 34. In these embodiments, the intermediate number $N_i$ can be constant from one discharge to another, from one mixer truck to another and the like.

Figure 5:
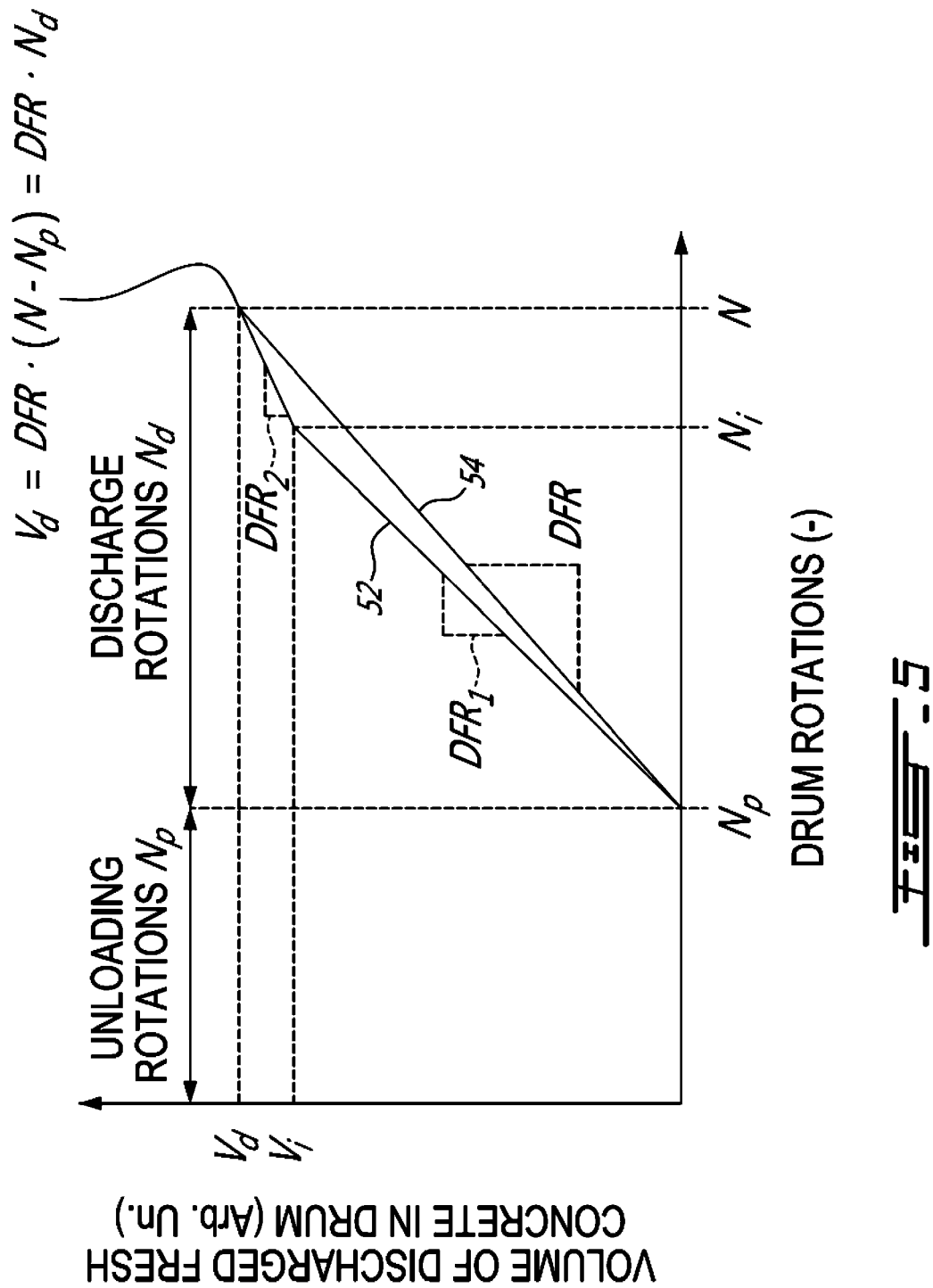
FIG. 5 is a graph showing volume of fresh concrete being discharged from the drum of FIG. 1 as function of discharge rotations of the drum, in accordance with an embodiment.

FIG. 5 shows the discharge volume value $V_D$ of fresh concrete as function of the discharge rotations. Similarly to FIG. 2, relation 52 takes into consideration the discharge flow rate variation data $DFR(N_d)$ whereas relation 54 does not as it involves a single discharge flow rate throughout the discharge rotations such as in the existing techniques. As can be seen, considering the variation in discharge flow rate as function of the discharge rotations can offer significant improvements for determining the discharge volume value $V_D$ as well.

In some other embodiments, the controller 34 can receive a signal indicative that the intermediate number $N_i$ of discharge rotations during said discharge rotations has been reached.

Such signal can be received from one or more discharge outlet sensors which are disposed at the discharge outlet 24 of the drum 16 and which are configured to sense the presence of fresh concrete at the discharge outlet 24 as the drum 16 rotates in the unloading direction. Examples of such discharge outlet sensors are described in greater detail below.

In some embodiments, the signal can be indicative that at least one of the inwardly protruding blades 22 arrives at the discharge outlet 24 only partially full of fresh concrete, thus hinting to the fact that the first discharge flow rate value $DFR_1$ should no longer be used for the rest of the discharge rotations to the benefit of the second discharge flow rate $DFR_2$.

Alternately, or additionally, the signal can be indicative that fresh concrete is discharged in a more or less discontinuous fashion at the discharge outlet 24 of the drum 16. For instance, one or more of these discharge outlet sensors can be configured to sense that fresh concrete is falling in a more or less discontinuous manner between one of the inwardly protruding blades 22 and a discharge chute 46 of the mixer truck 17, or to sense that fresh concrete falls in a more or less discontinuous manner on the discharge chute 46.

Figure 6:
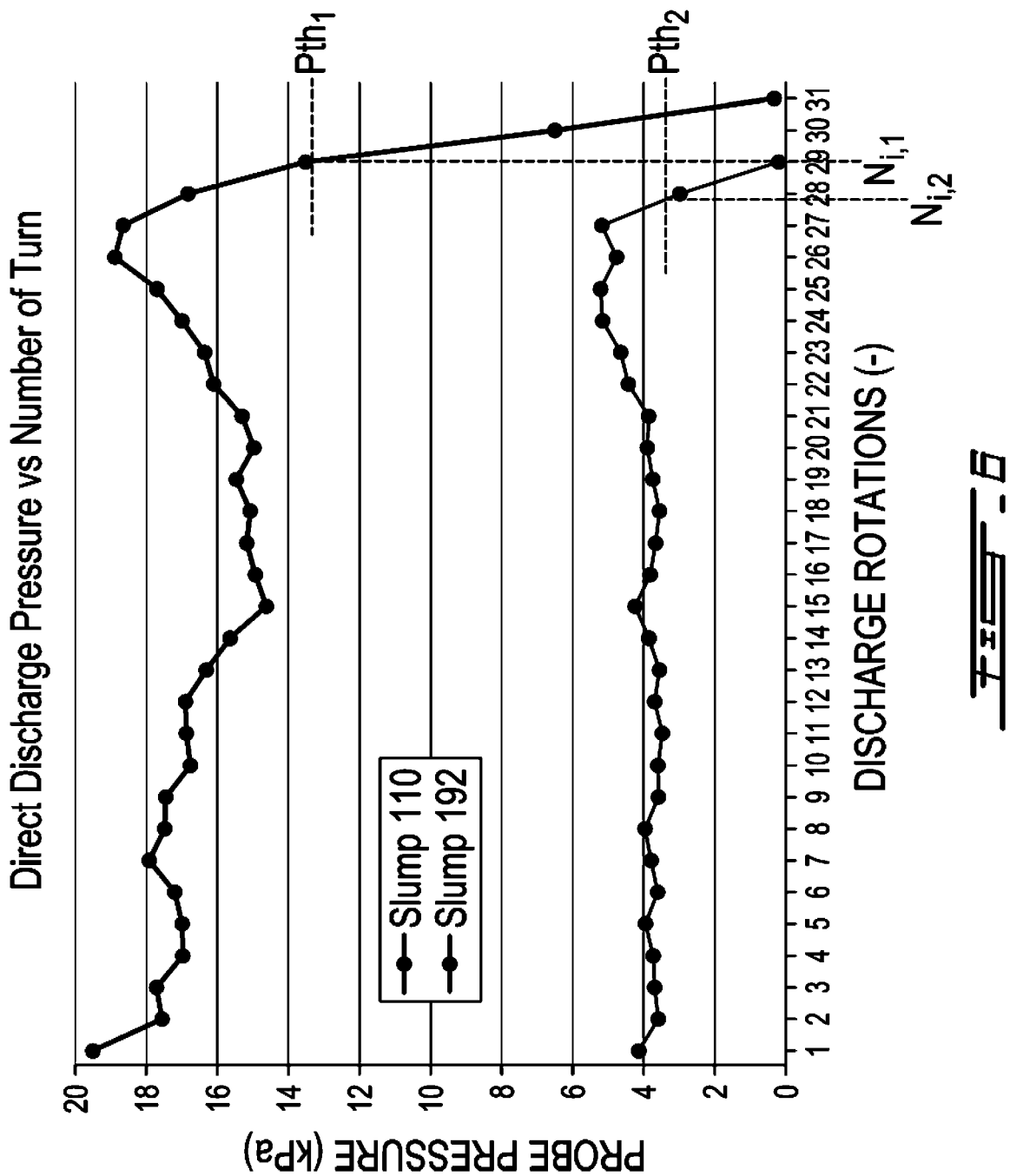
FIG. 6 is a graph showing probe pressure as received from a rheological probe mounted inside the drum of FIG. 1 as function of discharge rotations, in accordance with an embodiment.

In a specific embodiment, the signal can be received, not from the discharge outlet sensors but from the rheological probe 32. In this specific embodiment, the controller 34 receives a signal from the rheological probe 32 indicative of probe pressure values measured by the rheological probe 32 as the drum 16 rotates during the discharge rotations. An example of such probe pressure values is presented in FIG. 6. As depicted, the controller 34 can be configured to determine that the intermediate number $N_i$ of discharge rotations has been reached when the probe pressure values measured by the rheological probe 32 as the drum 16 rotates are below a given probe pressure value threshold. For instance, for a fresh concrete having a first composition, the probe pressure value as measured by the rheological probe 32 goes below a first probe pressure value threshold $P_{th,1}$ when the drum 16 is at about the $29^{th}$ discharge rotation. Accordingly, the intermediate number $N_i$ of discharge rotations in this case would likely be about 29. Similarly, for a fresh concrete having a second composition, the probe pressure value as measured by the rheological probe 32 goes below a second probe pressure value threshold $P_{th,2}$ when the drum 16 is at about the $27.5^{th}$ discharge rotation. Accordingly, the intermediate number $N_i$ of discharge rotations in this case would likely be about 27.5. A similar signal can be received from the hydraulic pressure sensor 30 in some other embodiments.

In the examples described above, the discharge flow rate variation data DFR ($N_d$) include different discharge rate values for different ranges of the discharge rotations. However, in some other embodiments, the discharge flow rate variation data DFR ($N_d$) can include a mathematical relation (e.g., linear, curvilinear) in which the discharge flow rate varies as function of the discharge rotations. For instance, the discharge flow rate discharge flow rate variation data DFR($N_d$) can include a combination of both, i.e., they can include a specific discharge flow rate value $DFR_1$ for a first range of the discharge rotations and a function DFR($N_d$) for a subsequent range of the discharge rotations, or vice versa.

The controller 34 can be provided as a combination of hardware and software components. The hardware components can be implemented in the form of a computing device 700, an example of which is described with reference to FIG. 7. Moreover, the software components of the controller 34 can be implemented in the form of one or more software applications, examples of which are described with reference to FIGS. 8 and 12.

Figure 7:
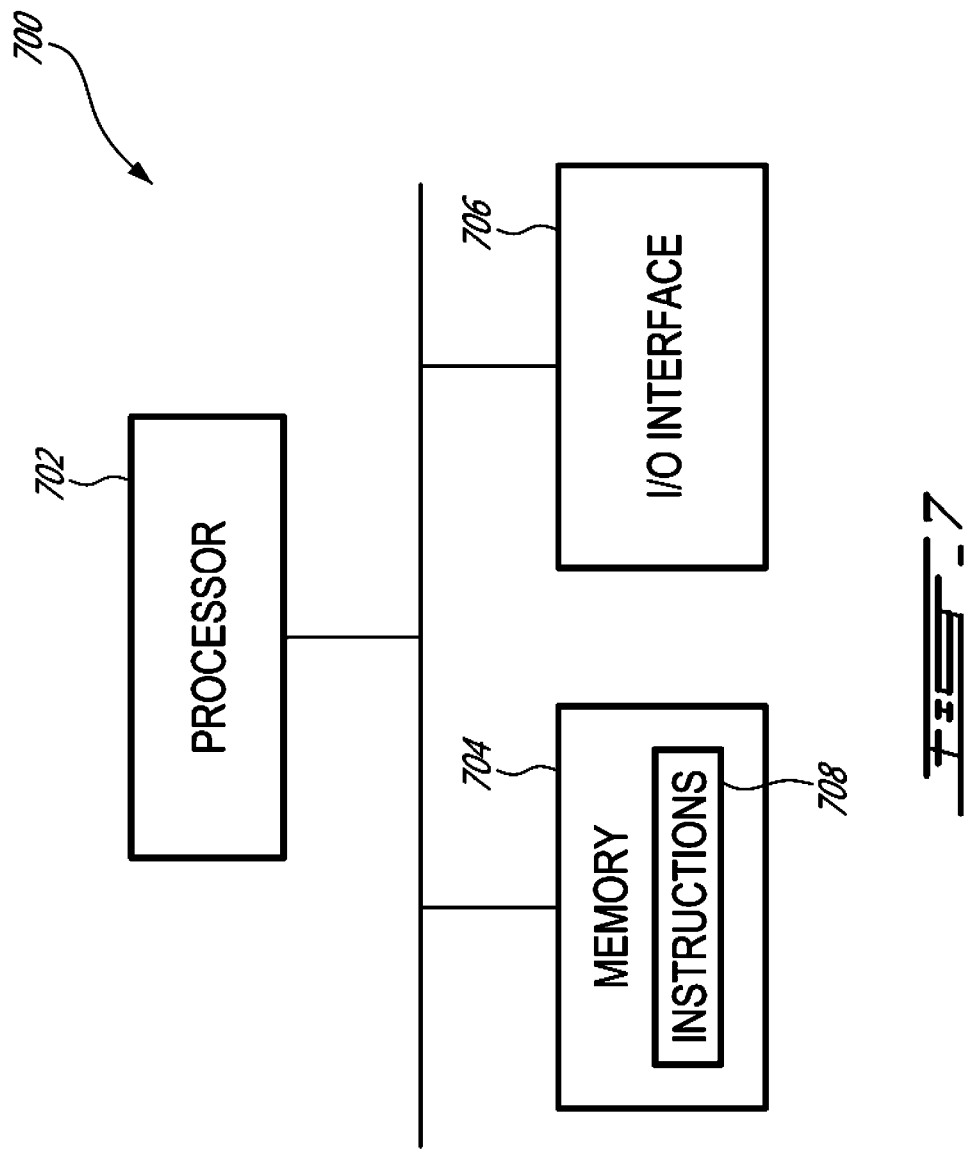
FIG. 7 is a schematic view of an example of a computing device of a controller of FIG. 1, in accordance with an embodiment.

Referring now to FIG. 7, the computing device 700 can have a processor 702, a memory 704, and I/O interface 706. Instructions 708 for determining the discharged volume value $V_d$ and/or the remaining volume value $V_R$ can be stored on the memory 704 and accessible by the processor 702.

The processor 702 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 704 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 706 enables the computing device 700 to interconnect with one or more input devices, such as an indication of a viscosity (e.g., type of, viscosity value, viscosity range) of the fresh concrete 12 inside the drum 16, an indication of a volume of fresh concrete 12 that is initially loaded in the drum 16 at the concrete production plant, an indication of the number of rotations to be made in the mixing direction, an indication of the number of rotations to be made in the unloading direction and/or an indication of a rotation speed of the drum 16, or with one or more output devices, such as the given number $N_d$ of discharge rotations, the priming number $N_p$ of unloading rotations, the total number $N_T$ of discharge rotations, the discharged volume value $V_d$, the remaining volume value $V_R$ and the like.

Each I/O interface 706 enables the controller 34 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 8:
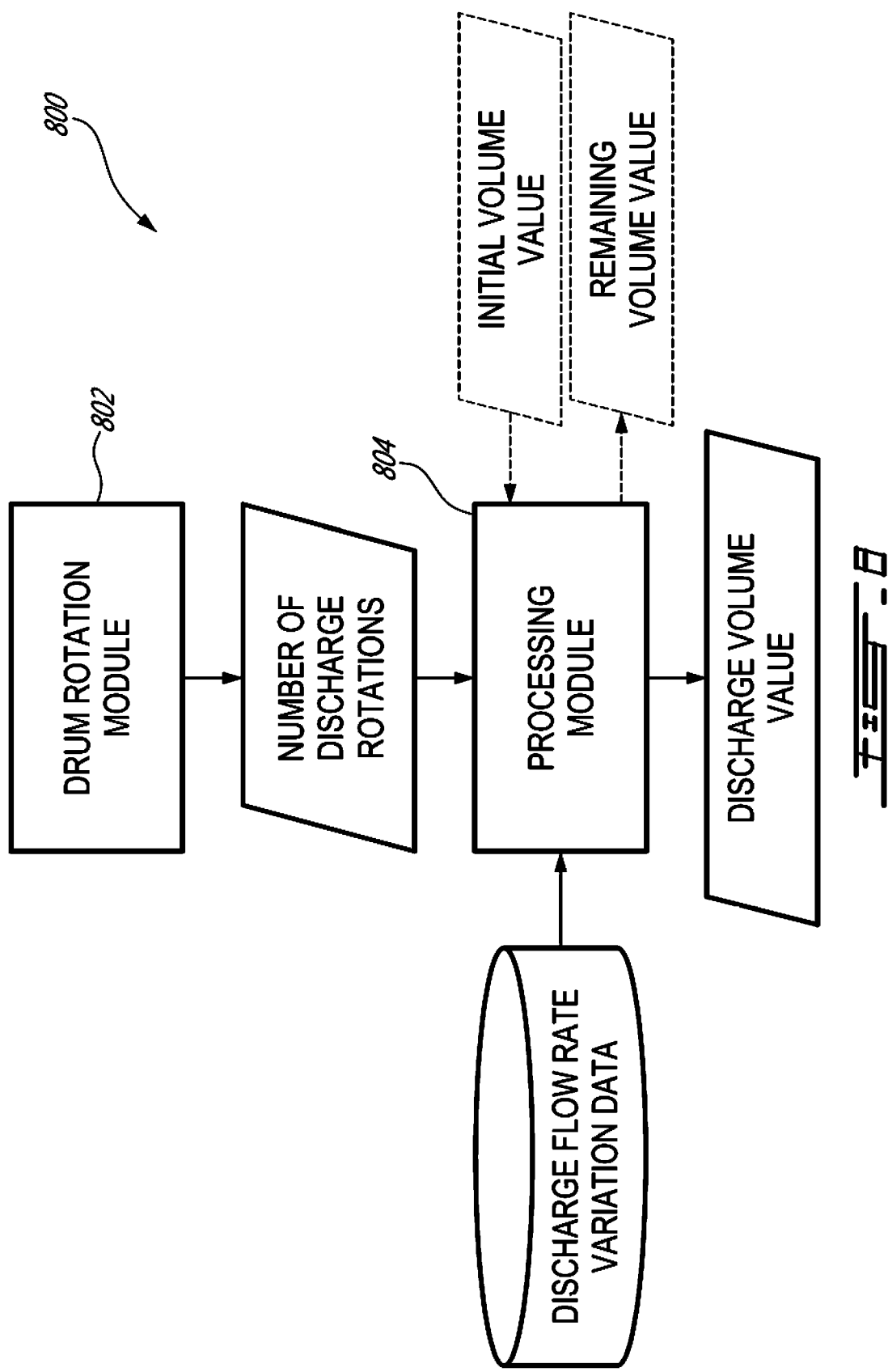
FIG. 8 is a schematic view of an example of a software application of the controller of FIG. 1 being configured to perform the method of FIG. 4, in accordance with an embodiment.

Referring now to FIG. 8, the software application 800 is configured to receive data being indicative of the instructions 708 and to determine the instructions 708 upon processing the data. In some embodiments, the software application 800 is stored on the memory 704 and accessible by the processor 702 of the computing device 700.

As shown in this specific embodiment, the software application 800 has a drum rotation module 802 which is communicatively coupled to a processing module 804.

The drum rotation module 802 is configured to receive data from the hydraulic pressure sensor 30, the rheological probe 32 and/or any other suitable rotation sensor and to determine a number $N_d$ of discharge rotations. The number $N_d$ of discharge rotations can thus be transmitted, in a wired or wireless fashion, to the processing module 804. In some specific embodiments, the drum rotation module 802 can receive one or more signal from discharge outlet sensors to indicate when the given number $N_d$ of discharge rotations starts and ends.

The processing module 804 is configured to receive the discharge flow rate variation data DFR($N_d$) which can be stored on the memory 704 or any other memory accessible by the software application 800. Once the number $N_d$ of discharge rotations is received from the drum rotation module 802 and the discharge flow rate variation data DFR($N_d$) from the memory 704, the processing module 804 is configured to determine the discharged volume value $V_d$ based on the number $N_d$ of discharge rotations and on the discharge flow rate variation data DFR($N_d$).

The processing module 804 can also be configured to receive the initial volume value $V_I$, in which case the processing module 804 can determine the remaining volume value $V_R$ based on the initial volume value $V_I$, on the number $N_d$ of discharge rotations and on the discharge flow rate variation data DFR($N_d$). Alternately or additionally, the processing module 804 can determine the remaining volume value $V_R$ based on the initial volume value $V_I$, on a previously determined discharged volume value $V_d$.

The computing device 700 and the software application 800 described above are meant to be examples only. Other suitable embodiments of the controller 34 can also be provided, as it will be apparent to the skilled reader.

Figure 9:
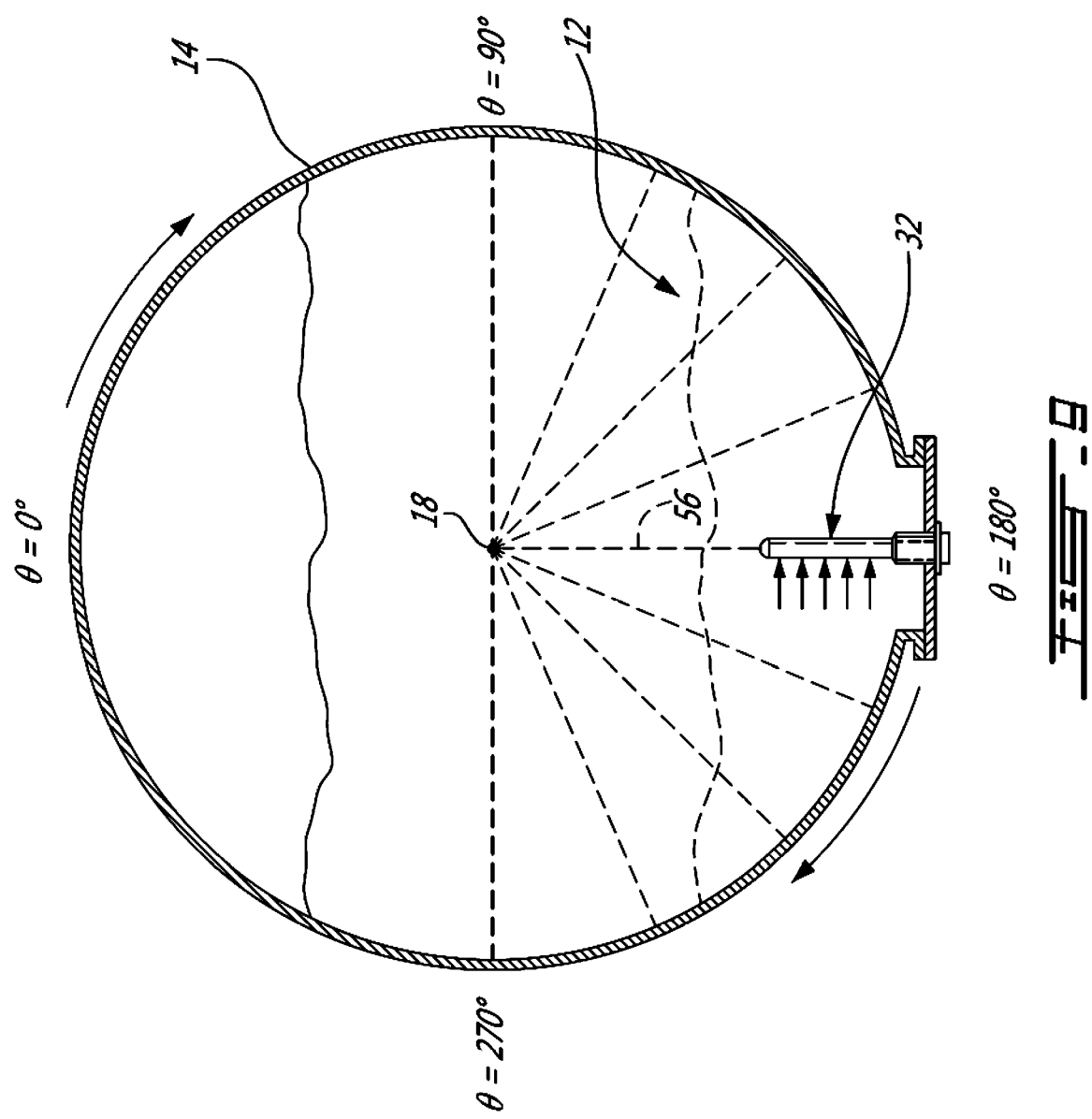
FIG. 9 is a sectional view of the system of FIG. 1, taken along line 9-9 of FIG. 1.

Referring now to FIG. 9, a sectional view of the drum 16 taken along line 9-9 of FIG. 1 is shown. As depicted, the rheological probe 32 extends in a radial orientation 56 of the drum 16 and reaches a plurality of circumferential positions θ as the drum 16 rotates about the rotation axis 18. In this way, the rheological probe 32 can be used to measure probe pressure values as the rheological probe 32 is moved circumferentially in the fresh concrete 12 by the rotation of the drum 16 about the rotation axis 18.

More specifically, in this illustrated example, the rheological probe 32 is at a circumferential position θ of 0° when at the top of the drum 16, at a circumferential position of 90° when at the right of the drum 16, at a circumferential position of 180° when at the bottom of the drum 16, and at a circumferential position of 270° when at the left of the drum 16. Such definition of the circumferential positions θ is exemplary only as the circumferential positions θ could have been defined otherwise depending on the embodiment.

Figure 10:
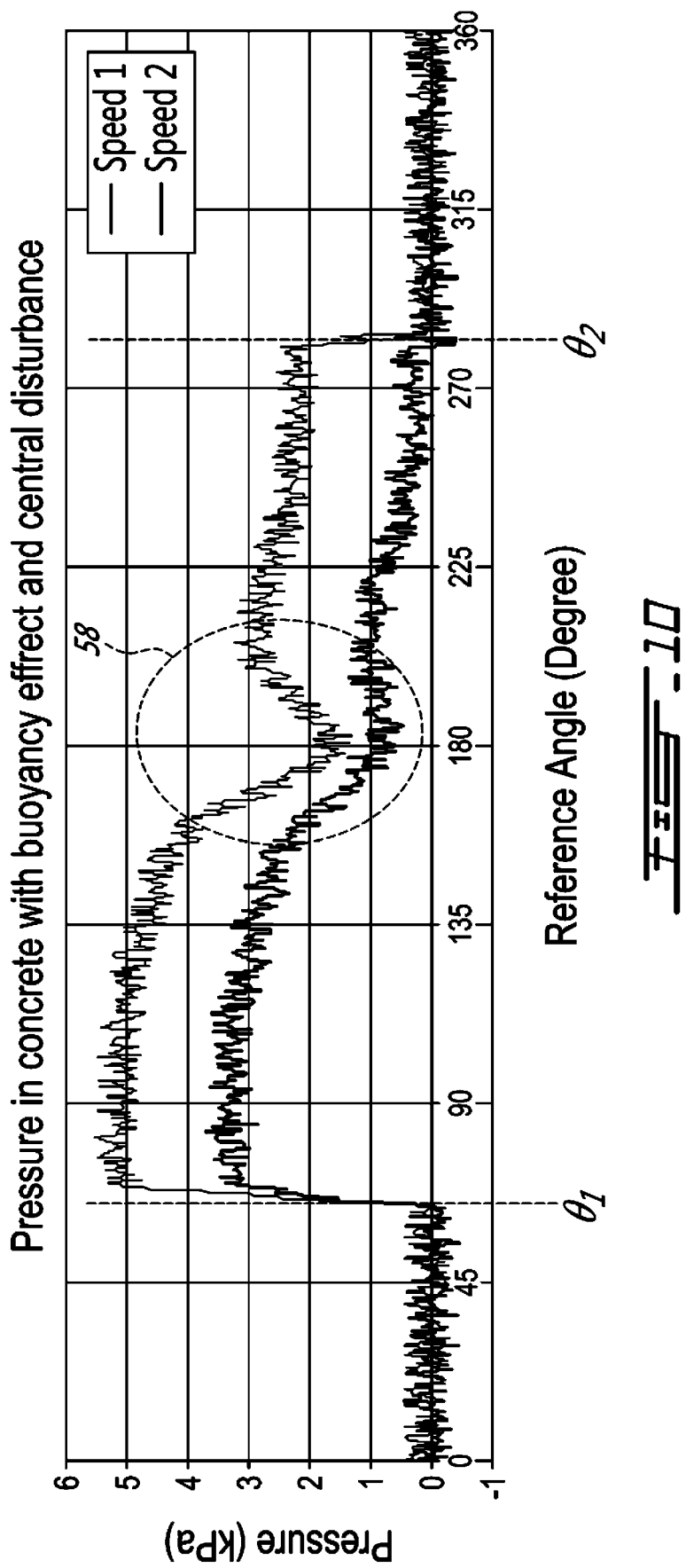
FIG. 10 is a graph showing probe pressure as received from the rheological probe mounted inside the drum of FIG. 1 as function of circumferential position during a single rotation of the drum.

FIG. 10 is an example of a graph showing, for two different rotation speeds of a drum 16, probe pressure values as measured by the rheological probe 32 as the drum 16 rotates, with discrepancies 58 for pressure values measured in the vicinity of the bottom of the drum 16.

Now, as can be understood, the volume of fresh concrete 12 remaining inside the drum 16 after a partial discharge can be measured using the probe pressure values as exemplified in FIG. 10. Indeed, by measuring the difference between a first circumferential position $\theta_1$ indicative of the circumferential position at which the rheological probe 32 enters the fresh concrete 12 and a second circumferential position $\theta_2$ indicative of the circumferential position at which the rheological probe 32 exits the fresh concrete 12, the remaining volume value $V_R$ of fresh concrete remaining inside the drum 16 after a partial discharge can be determined.

Referring now more specifically to FIG. 11, there is described a method 1100 of determining a first discharge flow rate value $DFR_1$ being indicative of a discharge flow rate at which the fresh concrete has been discharged during a previous partial discharge. As can be understood, the method 1100 can be performed by the controller 34 and is described with reference to the system 10 of FIG. 1 for ease of reading.

At step 1102, the controller 34 obtains an initial volume value $V_I$ indicative of an initial volume of the fresh concrete 12 inside the drum 16 prior to a partial discharge.

In some embodiments, the step 1102 includes receiving the initial volume value $V_I$ from a computer-readable memory accessible by the controller 34 such as memory 604.

In some other embodiments, the step 1102 includes, prior to the partial discharge, rotating the drum in the mixing direction for a given period of time and receiving a plurality of probe pressure values indicative of pressure exerted on the rheological probe 32 mounted inside the drum 16 and immerged in the fresh concrete 12 as the drum 16 rotates in the mixing direction. After these rotations, the controller 34 can determine the initial volume value $V_I$ indicative of the volume of fresh concrete 12 initially inside the drum 16 based on the so-received probe pressure values.

At step 1104, the controller 34 instructs the driving device 28 to perform a partial discharge by rotating the drum 16 in the unloading direction until fresh concrete is discharged at the discharge outlet 24 of the drum 16 and maintaining said rotating for a given number $N_d$ of discharge rotations thereafter.

At step 1106, the controller 34 instructs the driving device 28 to rotate the drum 16 in the mixing direction, opposite to the unloading direction, for a given period of time $\Delta t$ and receiving a plurality of probe pressure values indicative of pressure exerted on the rheological probe 32 mounted inside the drum 16 and immerged in the fresh concrete 12 as the drum rotates 16 in the mixing direction. For instance, the rotation of the drum 16 in the mixing direction can include rotating the drum 16 for at least three full rotations in the mixing direction.

At step 1108, the controller 34 determines a remaining volume value $V_R$ indicative of a volume of fresh concrete remaining in the drum 16 after the partial discharge based on said plurality of probe pressure values.

For instance, the remaining volume value $V_R$ can be determined based on a known geometry of the drum, on a known tilt of the rotation axis 18, and on a difference between a first circumferential position $\theta_1$ at which the rheological probe 32 enters the fresh concrete and a second circumferential position $\theta_2$ at which the rheological probe 32 exits the fresh concrete, as determined from the probe pressure values.

At step 1110, the controller 34 determines the first discharge flow rate value $DFR_1$ indicative of the discharge flow rate during the partial discharged based on the initial volume value $V_I$, on the given number $N_d$ of discharge rotations and on the previously determined remaining volume value $V_R$.

In some embodiments, the determination of the first discharge flow rate value $DFR_1$ includes the controller 34 calculating the first discharge flow rate value $DFR_1$ using a relation equivalent to the following relation:

$$DFR_1=(V_I-V_R)/N_d,$$

wherein $DFR_1$ denotes the first discharge rate value, $V_I$ denotes the initial volume value, $V_R$ denotes the remaining volume value, and $N_d$ denotes the given number of discharge rotations.

It is intended here that the step 404 of method 400 can involve the method 1100 in determining one or more of the discharge flow rates included in the discharge flow rate variation data $DFR(N_d)$. For instance, the first discharge rate value $DFR_1$ determined with reference to the method 1100 can be one of the first discharge flow rate value $DFR_1$ determined above with reference to the method 400.

Referring now to FIG. 12, the software application 1200 is configured to receive data being indicative of the instructions 708 and to determine the instructions 708 upon processing the data. In some embodiments, the software application 1200 is stored on the memory 704 and accessible by the processor 702 of the computing device 700.

As shown in this specific embodiment, the software application 1200 has a drum rotation module 1202 and a rheological probe module 1206 which are both communicatively coupled to a processing module 1204.

The drum rotation module 1202 is configured to receive data from the hydraulic pressure sensor 30, the rheological probe 32 and/or any other suitable rotation sensor and to determine a number $N_d$ of discharge rotations. The number $N_d$ of discharge rotations can thus be transmitted, in a wired or wireless fashion, to the processing module 1204.

The rheological probe module 1206 is configured to receive probe pressure values from the rheological probe 32 and to transmit them to the processing module 1204.

The processing module 1204 is configured to determine the remaining volume value $V_R$ based on the received probe pressure values and to obtain the initial volume value $V_I$.

The processing module 1204 is configured to determine the first discharge flow rate $DFR_1$ based on the number $N_d$ of discharge rotations received from the drum rotation module 1202, on the initial volume value $V_I$ and on the remaining volume value $V_R$.

FIG. 13 is an enlarged view of the discharge outlet 24 of the drum 16 of FIG. 1. As depicted, discharge outlet sensors 60, 62, 64 and 66 are disposed at the discharge outlet 24 of the drum 16. As shown, each inwardly protruding blade 22 acts as an Archimedes' screw and creates a series of small reservoirs that each collects a portion of the fresh concrete 12 from the bottom part of the drum 16 and brings it to the discharge outlet 24 of the drum 16.

In this embodiment, the controller 34 (shown in FIG. 1) is configured to receive one or more signals from the one or more of the discharge outlet sensors 60, 62, 64 and 66 during rotation of the drum 16.

More specifically, the discharge outlet sensors 60, 62, 64 and 66 are configured to sense the presence of the fresh concrete 12 at the discharge outlet 24 as the drum 16 rotates in the unloading direction so that one or more parameters be determined based on the received signal(s) by the controller 34.

As can be understood, the discharge outlet sensors 60, 62, 64 and 66 are communicatively coupled to the controller 34, wiredly and/or wirelessly.

In some embodiments, the parameter that is determined includes a priming number $N_p$ of discharge rotations. In these embodiments, the priming number $N_p$ of discharge rotations is indicative of the number of discharge rotations required for the fresh concrete 12 to reach the discharge outlet 24.

For instance, the discharge outlet sensors 60 and 62 can be configured to monitor the presence of fresh concrete 12 in the inwardly protruding blades 22 as the inwardly protruding blades 12 successively reach the discharge outlet 24.

In this case, the priming number $N_p$ of discharge rotations indicates the number of discharge rotations required for at least one of the inwardly protruding blades 22, or corresponding small reservoirs, to arrive at the discharge outlet 24 with at least some fresh concrete therein.

In some embodiments, the discharge outlet sensor 60 is mounted to a loading hopper 48 of the mixer truck 17. As can be understood, the discharge outlet sensor 60 monitors a distance d between the discharge outlet sensor 60 and the fresh concrete 12 inside an upper one of the inwardly protruding blades 22. When the inwardly protruding blades 22 include one spiral blade, the discharge outlet sensor 60 can be used to obtain a signal such as the one shown in FIG. 14A whereas when the inwardly protruding blades 22 include two spiral blades, the discharge outlet sensor 60 can be used to obtain a signal such as the one shown in FIG. 14B. As shown, the period of the signal of FIG. 14A is twice the period of the signal of FIG. 14B. FIG. 14C shows a signal received from the discharge outlet sensor 60 as fresh concrete is brought from the bottom of the drum 16 to the discharge end 24. Accordingly, one can determine the priming number $N_p$ of discharge rotations based on this signal to be 1.3 in this example. The discharge outlet sensor 60 can include a laser source and/or a detector such as a camera in these embodiments, in which case the laser beam can be pointed towards a location that is just before where the fresh concrete 12 would exit the drum 16 at the discharge end 24.

In some other embodiments, the discharge outlet sensor 62 is mounted to an internal wall of the drum 16 in close proximity with an upper one of the inwardly protruding blades 22. Similarly to the discharge outlet sensor 60, the discharge outlet sensor 62 can be used to sense the presence of the fresh concrete in the upper one of the inwardly protruding blades, and thus to determine the priming number $N_p$ of discharge rotations.

In other cases, the discharge outlet sensor 64 is configured to monitor the presence of the fresh concrete 12 falling between the inwardly protruding blades 22 and the discharge chute 46 of the discharge outlet 24. In these cases, the priming number $N_p$ of discharge rotations indicating the number of discharge rotations required for fresh concrete to be sensed falling between the inwardly protruding blades 22 and the discharge chute 46. As shown, the discharge outlet sensor 64 is mounted to a discharge hopper 47 of the mixer truck 17.

In a specific embodiment, the discharge outlet sensor 64 is provided in the form of a motion detector and measures the distance and/or simply detects the nearby presence of the falling concrete between the drum 16 and the discharge chute 46. In this embodiment, the motion detector can be self-calibrating when the drum 16 rotates in the mixing direction, when it is certain that no fresh concrete is falling between the discharge outlet 24 and the discharge chute 46.

In another specific embodiment, the discharge outlet sensor 64 is provided in the form of a transceiver emitting an optical, radio and/or acoustic signal where fresh concrete is supposed to be falling and to receive a reflection of the optical, radio and/or acoustic signal based on whether fresh concrete is falling or not. An example of such a sensor includes the type of sensors which are installed on car bumpers.

In alternate cases, the discharge outlet sensor 66 is configured to monitor the presence of fresh concrete as the fresh concrete 12 falls on the discharge chute 46 of the mixer truck 17. As such, the priming number $N_p$ of discharge rotations indicates the number of discharge rotations required for fresh concrete to actually fall on the discharge chute 46.

As can be understood, the discharge outlet sensors 60, 62, 64 and 66 can be used to determine the intermediate number $N_i$ of discharge rotations discussed above. Indeed, the intermediate number $N_i$ of discharge rotations can be determined when the signal is indicative that the discharge of the fresh concrete 12 at the discharge outlet 24 is discontinuous.

In some embodiments, the intermediate number $N_i$ of discharge rotations is indicative of the number of discharge rotations required for the fresh concrete to be discharged at the discharge outlet in a discontinuous fashion.

In these embodiments, the discharge outlet sensors 60 and 62 are configured to monitor a filling level of fresh concrete in the inwardly protruding blades 22 as the inwardly protruding blades 22 successively reach the discharge outlet 24. In these embodiments, the intermediate number $N_i$ of discharge rotations is indicative of the number of discharge rotations required for the filling level to be below a filling level threshold thereby indicating that at least one of the inwardly protruding blades 22 arrives at the discharge outlet 24 only partially full of fresh concrete. As can be understood, in some embodiments, the filling level of the inwardly protruding blades 22 as sensed by the discharge outlet sensors 60 and 62, or any other discharge outlet sensors, can be used to determine a current discharge flow rate indicative of the volume of fresh concrete being discharged per discharge rotations.

In alternate embodiments, the discharge outlet sensor 64 is configured to monitor a discontinuity level in a discharge flow rate of the fresh concrete falling between the inwardly protruding blades 22 and the discharge chute 46. In these embodiments, the intermediate number $N_i$ of discharge rotations is indicative of the number of discharge rotations required for the discontinuity level to be above a discontinuity level threshold thereby indicating that fresh concrete is discharged in a discontinuous fashion at the discharge outlet 24 of the drum 16.

In some other embodiments, the discharge outlet sensor 66 is configured to monitor a discontinuity level of the fresh concrete as the fresh concrete falls on the discharge chute 46 of the discharge outlet 24 of the drum 16. In these embodiments, the intermediate number $N_i$ of discharge rotations is indicative of the number of discharge rotations required for the discontinuity level to be above a discontinuity level threshold thereby indicating that fresh concrete is discharged on the discharge chute 46 in a discontinuous fashion.

Referring now to FIG. 15, there is described a method 1500 for determining at least one parameter characterizing delivery of fresh concrete using the mixer truck 17. As can be understood, the method 1500 can be performed by the controller 34 and is described with reference to the system 10 of FIG. 1 for ease of reading.

At step 1502, the controller 34 instructs the driving device 28 to discharge a volume of the fresh concrete 12 from the drum 16 by rotating the drum 16 in the unloading direction while monitoring a given number $N_d$ of unloading rotations.

At step 1504, the controller 34 monitors the presence of the discharged fresh concrete at the discharge outlet 24 as the drum 16 rotates in the unloading direction based on signal received from one or more of the discharge outlet sensors 60, 62, 64 and 66.

At step 1506, the controller 34 determines one or more parameters characterizing the delivery of the fresh concrete using the mixer truck 17 based on the given number of $N_d$ unloading rotations and on the signal received from one of the discharge outlet sensors 60, 62, 64 and 66.

In some embodiments, the parameters include a priming number $N_p$ of unloading rotations indicating a number of rotations of the drum in the unloading direction for the fresh concrete 12 to reach the discharge outlet 24 based on the signal received from one of the discharge outlet sensors 60, 62, 64 and 66.

In some other embodiments, the parameters include a total number $N_T$ of discharge rotations based on said monitoring. The total number $N_T$ of discharge rotations indicates a number of discharge rotations of the drum in the unloading direction that is required for the drum to be emptied of fresh concrete 12 after or including said priming number $N_p$ of unloading rotations.

It is intended that discharge outlet sensors 60, 62, 64 and 66 need not to be mounted to every mixer trucks. For instance, in some embodiments, the discharge outlet sensors 60, 62, 64 and 66 can be used to collect calibration data indicative of the priming number $N_p$ of unloading rotations and/or the total number $N_T$ of discharge rotations for different mixer trucks of the same type, different types of mixer trucks, different compositions of fresh concrete, different tilt of the mixer truck and so forth.

As can be understood, the examples described above and illustrated are intended to be exemplary only. For instance, the drum does not need to be rotatably mounted to a mixer truck. For instance, the drum can be part of a stationary concrete mixer such as those provided in concrete production plants. In some alternate embodiments, the rheological probe can be any type of internal probe, i.e. any probe which is mounted inside the drum. Moreover, various materials can be handled in a manner similar to the way fresh concrete is handled in a mixer truck. The material can be in the form of a suspension of aggregates in a rheological substance, such as fresh concrete, but the materials can also be bulk aggregates such as sand, gravel, crushed stone, slag, recycled concrete and geosynthetic aggregates, for instance. The scope is indicated by the appended claims.

What is claimed is:

1. A ready-mix truck comprising:
a wheeled frame;
a drum rotatably mounted to the wheeled frame for receiving a material, the drum having inwardly protruding blades mounted inside the drum which, when the drum is rotated in an unloading direction, force the material received inside the drum towards a discharge outlet of the drum;
a discharge outlet sensor disposed at the discharge outlet of the drum and being configured to sense the presence of the material at the discharge outlet as the drum rotates in the unloading direction; and
a controller communicatively coupled with the discharge outlet sensor, the controller having a processor and a memory having stored thereon instructions that when executed by the processor perform the steps of:
receiving a signal from the discharge outlet sensor;
detecting arrival of the material at the discharge outlet as the drum rotates in the unloading direction based on the received signal; and
determining a parameter based on the detected arrival of the material at the discharge outlet.

2. The ready-mix truck of claim 1 wherein said parameter is a priming number of discharge rotations, the priming number of discharge rotations being indicative of the number of discharge rotations required for the material to reach the discharge outlet.

3. The ready-mix truck of claim 2 wherein the discharge outlet sensor is configured to monitor the presence of material in the inwardly protruding blades as the inwardly protruding blades successively reach the discharge outlet, the priming number of discharge rotations indicating the number of discharge rotations required for at least one of the inwardly protruding blades to arrive at the discharge outlet with at least some material therein.

4. The ready-mix truck of claim 2 wherein the discharge outlet sensor is configured to monitor the presence of the material when material is falling between the inwardly protruding blades and a discharge chute of the discharge outlet, the priming number of discharge rotations indicating the number of discharge rotations required for material to be falling between the inwardly protruding blades and the discharge chute.

5. The ready-mix truck of claim 1 wherein said parameter is an intermediate number of discharge rotations, the intermediate number of discharge rotations being indicative of the number of discharge rotations required for the material to be discharged at the discharge outlet in a discontinuous fashion.

6. The ready-mix truck of claim 5 wherein the discharge outlet sensor is configured to monitor a filling level of material in the inwardly protruding blades as the inwardly protruding blades successively reach the discharge outlet, the intermediate number of discharge rotations being indicative of the number of discharge rotations required for the filling level to be below a filling level threshold thereby indicating that at least one of the inwardly protruding blades arrives at the discharge outlet only partially full of material.

7. The ready-mix truck of claim 6 wherein the controller is configured to perform a step of determining a discharge flow rate value indicative of the volume of material being discharged from the drum per discharge rotation based on the monitored filling level.

8. The ready-mix truck of claim 5 wherein the discharge outlet sensor is configured to monitor a discontinuity level in a discharge flow rate of the material falling between the inwardly protruding blades and a discharge chute of the discharge outlet of the drum, the intermediate number of discharge rotations being indicative of the number of discharge rotations required for the discontinuity level to be above a discontinuity level threshold thereby indicating that material is discharged in a discontinuous fashion at the discharge outlet of the drum.

9. A method for determining parameter characterizing delivery of material using a mixer truck, the mixer drum having a rotatable drum having inwardly protruding blades mounted inside the drum which, when the drum is rotated in an unloading direction, force the material towards a discharge outlet of the drum, the method comprising:
discharging a volume of the material from the drum by rotating the drum in the unloading direction while monitoring a given number of unloading rotations;
using a discharge outlet sensor disposed at the discharge outlet of the drum, monitoring the presence of the discharged material at the discharge outlet as the drum rotates in the unloading direction; and using a controller being communicatively coupled to the discharge outlet sensor, detecting arrival of the material at the discharge outlet based on said monitoring and determining a parameter characterizing the delivery of the material based on the given number of unloading rotations at said arrival of the material.

10. The method of claim 9 wherein said parameter is a priming number of unloading rotations indicating a number of rotations of the drum in the unloading direction for the material to reach the discharge outlet based on said monitoring.

11. The method of claim 9 wherein said parameter is a total number of discharge rotations based on said monitoring, the total number of discharge rotations indicating a number of discharge rotations of the drum in the unloading direction that is required for the drum to be emptied of material after said priming number of unloading rotations.

12. The method of claim 9 further comprising, using the controller, monitoring a filling level of the material in the inwardly protruding blades as the inwardly protruding blades successively reach the discharge outlet, said parameter being a discharge flow rate value indicative of the volume of material being discharged from the drum per discharge rotation based on the monitored filling level.

13. The method of claim 9 wherein the material is fresh concrete.

* * * * *